United States Patent
Kim et al.

(10) Patent No.: US 11,478,579 B2
(45) Date of Patent: Oct. 25, 2022

(54) APPARATUS AND METHOD FOR MICROWAVE THERAPY FOR BLOOD CANCER TREATMENT

(71) Applicant: KWANGWOON UNIVERSITY INDUSTRY-ACADEMIC COLLABORATION FOUNDATION, Seoul (KR)

(72) Inventors: Nam-Young Kim, Gwangju-si (KR); Eun Seong Kim, Gwangju-si (KR)

(73) Assignee: KWANGWOON UNIVERSITY INDUSTRY-ACADEMIC COLLABORATION FOUNDATION, Seoul (KR)

( * ) Notice: Subject to any disclaimer, the term of this patent is extended or adjusted under 35 U.S.C. 154(b) by 295 days.

(21) Appl. No.: 16/957,576

(22) PCT Filed: Apr. 8, 2019

(86) PCT No.: PCT/KR2019/004146
§ 371 (c)(1),
(2) Date: Jun. 24, 2020

(87) PCT Pub. No.: WO2019/194666
PCT Pub. Date: Oct. 10, 2019

(65) Prior Publication Data
US 2020/0324039 A1  Oct. 15, 2020

(30) Foreign Application Priority Data

Apr. 6, 2018 (KR) .................. 10-2018-0040670
Apr. 4, 2019 (KR) .................. 10-2019-0039393

(51) Int. Cl.
*A61M 1/36*   (2006.01)
*A61M 1/34*   (2006.01)

(52) U.S. Cl.
CPC ........ *A61M 1/3681* (2013.01); *A61M 1/3413* (2013.01)

(58) Field of Classification Search
CPC .... A61M 1/16; A61M 1/3413; A61M 1/3472; A61M 1/3678; A61M 1/3681
See application file for complete search history.

(56) References Cited

FOREIGN PATENT DOCUMENTS

| JP | 09-511685 A | 11/1997 |
|----|-------------|---------|
| JP | 2005-074342 A | 3/2005 |

(Continued)

OTHER PUBLICATIONS

International Search Report for PCT/KR2019/004146 dated Jul. 4, 2019 [PCT/ISA/210].

(Continued)

*Primary Examiner* — Dirk R Bass
(74) *Attorney, Agent, or Firm* — Sughrue Mion, PLLC

(57) ABSTRACT

A microwave therapy apparatus and method for blood cancer treatment is disclosed. The microwave therapy apparatus for blood cancer treatment includes a plurality of porous anodic aluminum oxide (AAO) filters or a plurality of porous glass filters provided in a dialyzer of a hemodialysis apparatus; a nanoflower filter provided downstream of the plurality of porous anodic aluminum oxide (AAO) filters or the plurality of porous glass filters in the blood tube; and an RF absorber provided downstream of the nanoflower filter to attract cancer cells thereto by generating a frequency of a predetermined band, wherein the blood, from which the cancer cells have been removed by an RF frequency and which includes normal blood cells that passed through the nanoflower filter, is circulated and supplied to a blood tube connected to a vein of the body of the blood cancer patient.

19 Claims, 15 Drawing Sheets

(56) References Cited

FOREIGN PATENT DOCUMENTS

| KR | 10-0531748 B1 | 11/2005 |
| KR | 10-2010-0102454 A | 9/2010 |
| KR | 10-1081114 B1 | 11/2011 |
| KR | 10-2012-0042515 A | 5/2012 |
| KR | 10-2015-0041130 A | 4/2015 |
| KR | 10-1651937 B1 | 8/2016 |

OTHER PUBLICATIONS

Written Opinion of PCT/KR2019/004146 dated Jul. 4, 2019 [PCT/ISA/237].

Advantages of AAO filtering

- Chemical Stable and high structure strength
- The filtering hole size can be adjusted based on the abnormal cells.
- No harmful to human body Motility of melanoma skin cancer cells after 20 hour RF exposure

APPARATUS AND METHOD FOR MICROWAVE THERAPY FOR BLOOD CANCER TREATMENT

CROSS-REFERENCE TO RELATED APPLICATIONS

This application is a national stage application of PCT/KR2019/004146, which claims priorities to Korean Patent Application No. 10-2018-0040670, filed with the Korean Intellectual Property Office on Apr. 6, 2018, and Korean Patent Application No. 10-2019-0039393, filed with the Korean Intellectual Property Office on Apr. 4, 2019, the disclosures of which are herein incorporated by reference in their entireties.

FIELD OF THE INVENTION

The present invention relates to a microwave therapy apparatus and method for treating blood cancer, and more particularly, to a microwave therapy apparatus and method wherein: i) cancer cells having a larger diameter than normal blood cells that are being circulated through a blood tube are filtered out by size filtration using a plurality of porous anodic aluminum oxide (AAO) filters and a plurality of porous glass filters provided in a dialyzer of a hemodialysis apparatus for blood cancer therapy of a leukemia patient; ii) when the diameter size of cancer cells is equal to or smaller than the size of normal blood cells, the cancer cells are caused to adhere to the nanoflower filter and are removed by radiating an RF frequency of 450 MHz through turning on/off of an RF resonator of a microwave RF generator at regular intervals; and iii) cancer cells are removed by attraction to an RF absorber through generation of an RF frequency of 13.56 MHz, 27.12 MHz, 40.68 MHz or 54.12 MHz by the RF absorber provided on the upper side and lower side of the blood tube in an RF shield box in the hemodialyzer. The RF absorber means an RF cancer cell absorber.

BACKGROUND OF THE INVENTION

According to the Seoul National University Hospital, the bones of our body are involved in calcium regulation so that the body shape can be maintained and exercise is possible. Inside the bones, there are bone marrow tissues that are less dense than the bones, and the bone marrow tissue functions to make blood cells such as white blood cells, red blood cells, and platelets.

Blood comprises hemocytes and plasma. The hemocytes is composed of the blood cell components that take possession of approximately 45% of the total blood volume. Blood cells comprise white blood cells, red blood cell, and platelets.

White blood cells are blood cells that play an essential role in the destruction of infectious source and the production of antibodies for body's defense. Red blood cells are blood cells that carry oxygen and contain pigments (hemoglobins), and the number of red blood cells is the largest. Platelets are blood cells that prevent bleeding by the blood coagulation.

Plasma is a pale yellow, transparent, blood's liquid component that take possession of 55% of the total blood volume. It is mostly composed of water (91%), and contains blood coagulation factors, electrolytes, etc., which are essential for maintaining life. In addition, it contains plasma proteins (7%) such as albumin or blood coagulation factors, as well as electrolytes ($Na^+$, $Cl^-$, $HCO_3$, $K^+$, etc.), glucose, amino acids, lipids, vitamins, hormones, waste, etc.

Leukemia is a blood cancer that occurs in white blood cells among these blood cells. Leukemia is a kind of cancer and is also called 'marrow cancer' because it occurs due to abnormalities in hematopoietic cells. Leukemia belongs to a large category of blood cancer, along with lymphoma, multiple myeloma, and the like. Acute myeloid leukemia called 'blood cancer' is characterized by the appearance of leukemia cells in the bone marrow or blood.

Acute leukemia is a blood cancer in which white blood cells turn into malignant cells which proliferate in the bone marrow, spread throughout the body through the blood, and invade the liver, spleen, and lymph glands. Blood cancer shows various symptoms, such as anemia, reduced white blood cells, and reduced platelets, which interfere with the production of blood.

In leukemia, abnormal white blood cells (leukemia cells) proliferate excessively, and the production of normal white blood cells, red blood cells and platelets is suppressed. A decrease in the number of normal white blood cells can cause a decline in immunity and cause sepsis caused by bacterial infection, and a decrease in the number of red blood cells causes anemia symptoms (dizziness, headache, and difficulty in breathing). A decrease in the number of platelets causes a tendency to bleed. In addition, the hyperproliferative leukemia cells themselves may cause high fever, fatigue, bone pain, diarrhea, decreased consciousness, difficulty in breathing, and bleeding. Patients with leukemia are dangerous in life by above symptoms when not treated.

Leukemia is divided into acute and chronic leukemia according to the degree of cell differentiation, that is, the rate of exacerbation, and is divided into myeloid and lymphocytic leukemia depending on the origin of the cell. Leukemia is classified into four types: acute myeloid leukemia, acute lymphoblastic leukemia, chronic myeloid leukemia, and chronic lymphocytic leukemia.

Leukemia is a disease in which white blood cells proliferate neoplastically and diseased white blood cells leak into the blood.

Leukemia is a disease called hematopoietic tissue cancer, and has a low incidence, but once leukemia develops, it is life-threatening. The term "leukemia" was first proposed by R. Virchow who was the discoverer of the disease of white blood in 1846 because the blood looked white when the patient was autopsied.

Since then, the case in which white blood cells in the blood rarely increase while a change in tissue is the same has been called aleukemic leukemia. It is classified into lymphoid, myeloid, and monocytic leukemia according to the type of cells appearing in the blood, and is divided into acute and chronic leukemia according to the clinical course.

Although the cause of leukemia is unclear, leukemia is thought to be caused by radiation in light of the fact that it occurs frequently in atomic bomb victims or radiation workers.

In acute leukemia, the symptoms of both lymphoid and myeloid leukemia are rapid, showing high fever, stomatitis, gingivitis, necrotic angina, and bleeding tendency appears, which makes bleeding easier. Lymphoblasts or myeloblasts in the blood increase and red blood cells decrease, resulting in anemia. For treatment, adrenocortical hormones, folic acid antagonists, and purine antagonists are used, and transfusion is required.

Acute lymphocytic leukemia is a disease in which white blood cells of the lymphocytic system become malignant cells which then multiply in the bone marrow, spread to peripheral blood, and invade the liver, spleen, lymphatic system, cerebrum, cerebellum, spinal cord, and the like. This disease mainly affects children of 3 to 5 years old, and is known to be the most common child cancer. This disease is known that in this disease, the number of normal blood cells generally decreases. It is known that this disease is caused by exposure to carcinogens such as radiation exposure, benzene, toluene, and anticancer drugs.

Acute myeloid cell leukemia is acute leukemia of bone marrow cells, which is a malignant blood cancer that invades the cells of bone marrow granulocytes. It is called blood cancer in which leukemia cells multiply in bone marrow and spreads to peripheral blood or other organs.

Cause: the cause of leukemia is unclear, and is known to be exposure to carcinogens such as radiation exposure, benzene, toluene, and anticancer drugs.

Symptoms: the symptoms of leukemia include cold, body aches, fever, systemic fatigue, bleeding due to reduced platelets, anemia, paleness, hypertrophy of the gums, an increased size of the tumor in the liver and pancreas, and formation of lumps in soft skin flesh.

Treatment: treatment methods such as chemotherapy, radiation therapy, and hematopoietic stem cell transplantation are used.

Hematopoietic stem cell transplantation refers to transplanting stem cells that make blood, and bone marrow which is a centrosome of bone contains blood-producing cells that produce blood cell components such as red blood cells, white blood cells, and platelets (functioning to prevent bleeding). By the way, in order to fundamentally treat diseases having abnormalities in hematopoietic stem cells, such as leukemia, cancer cells are completely removed by high-dose chemotherapy and systemic radiation exposure, the bone marrow is completely evacuated, and then hematopoietic cells from healthy persons are transplanted thereto, whereby the hematopoietic stem cells live anew, divide and multiply to restore their ability to make blood.

In the past, the term "bone marrow transplantation" was used because hematopoietic stem cells were obtained from another person's bone marrow, but now, the term "hematopoietic stem cell transplantation" is used rather than "bone marrow transplantation" because hematopoietic stem cells can also be obtained from the blood of the umbilical cord (umbilical cord blood) or peripheral blood. Hematopoietic stem cells are stem cells that produce red blood cells, white blood cells and platelets, which make up the blood, and these hematopoietic stem cells are contained in bone marrow, peripheral blood, and umbilical cord blood.

Patients with blood cancer such as leukemia are unable to produce healthy blood, and thus their life is difficult to maintain. Therefore, a method is used in which healthy hematopoietic stem cells are provided from a donor having the same human leukocyte antigen (HLA) as a blood cancer patient so that the blood cancer patient can maintain his/her life by making blood having normal function from the healthy hematopoietic stem cells donated by the donor.

Chronic myelogenous leukemia is the most frequent type. The symptoms thereof include general malaise, poor appetite, etc., appear gradually, and show paleness of the skin, and lead to anemia. In addition, the liver and spleen become larger in size, and the pain of the bone, beating pain, fundus change, and vision loss occur. Furthermore, In addition, the number of platelets decreases, resulting in nasal bleeding, gingival hemorrhage, subcutaneous hemorrhage, and brain hemorrhage, and causes fever at the end. The number of white blood cells increases tremendously to 100,000 to 300,000 (a number that is several times 5,000 to 9,000 per $m^3$ for normal blood), and most of them are myelogenous leukocytes which are significantly less functional. For treatment, transfusion is used in combination with various anti-leukemia treatments and adrenal cortical hormones.

As the symptoms of chronic lymphocytic leukemia, the lymph nodes of the whole body swell sequentially, and this symptom is particularly pronounced in the cervical spine and inguinal regions. The size of the lymph nodes is about the size of an egg to the size of a fist. Anemia also occurs, the number of white blood cells increases, and most of the white blood cells are also of the lymphoid type. For treatment, administration of anti-leukemia treatments and transfusion are used, like the treatment of chronic myelogenous leukemia.

As Prior Art Document 1 related thereto, Korean Patent Registration No. 10-05317480000 discloses a leukemia diagnostic DNA chip for analyzing leukemia-specific gene abnormalities.

The leukemia diagnostic DNA chip provides a leukemia diagnostic DNA chip for analyzing leukemia-specific gene abnormalities, a method for preparing the DNA chip, and a genotyping kit for diagnosing leukemia including the DNA chip. The leukemia diagnostic DNA chip comprises: a gene probe for detecting leukemia-specific gene abnormalities, which consists of 18 to 25 nucleotides; a linker sequentially including 15 thymines (dTTP), 6 CH2 chains and an amine group, in which the 5' end of the gene probe is linked to the thymines; and a solid which has an aldehyde group bound to the surface thereof and on which the amine group of the linker is connected to the aldehyde group of the surface through a Schiff's base reaction. Using the genotyping kit, it is possible to quickly and accurately distinguish the genotype of leukemia. Thus, the genotyping kit may be widely used for early diagnosis of leukemia.

As Prior Art Document 2 related thereto, Korean Patent Registration No. 10-10811140000 discloses a leukemia diagnosis apparatus using DNA information and a method of operating the same.

A leukemia diagnosis apparatus using DNA information and a method of operating the same is disclosed. The leukemia diagnosis apparatus using DNA information comprises: a test value storage unit configured to store test information generated by digitizing the patient's DNA information; a reference storage unit configured to store a plurality of reference information formed of DNA information having the features of leukemia; a mask storage unit configured to store a plurality of masks including information on portions of the test information and the reference information, which are to be compared with each other; a comparison unit configured to compare the portions of the test information and the reference information with each other, which correspond to the masks, and check whether the portions are consistent with each other; an accumulator unit configured to generate coincidence information, which is the sum of the portions confirmed to be consistent by the comparison unit; and a determination unit configured to determine reference information having the largest amount of the coincidence information and display a diagnosis result corresponding to the reference information having the largest amount of the coincidence information.

As Prior Art Document 3 related thereto, Korean Patent Application Publication No. 10-2015-0041130 discloses leukemia classification using CPD data. Embodiments thereof encompass automated systems and methods for predicting an acute leukemia sub-type of an individual diagnosed with acute leukemia based on a biological sample obtained from blood of the individual. Exemplary techniques involve correlating aspects of direct current (DC) impedance, radiofrequency (RF) conductivity, and/or light measurement data obtained from the biological sample with an acute leukemic sub-type of the individual.

An automated system for predicting an acute leukemia sub-type of an individual diagnosed with acute leukemia based on a biological sample obtained from blood of the individual, the system comprising:

(a) an optical element having a cell interrogation zone; (b) a flow path configured to deliver a hydrodynamically focused stream of the biological sample toward the cell interrogation zone; (c) an electrode assembly configured to measure direct current (DC) impedance and radiofrequency (RF) conductivity of cells of the biological sample passing individually through the cell interrogation zone; (d) a light source oriented to direct a light beam along a beam axis to irradiate the cells of the biological sample individually passing through the cell interrogation zone; and (e) a light detection assembly optically coupled to the cell interrogation zone so as to measure light scattered by and transmitted through the irradiated cells of the biological sample, the light detection assembly configured to measure: (i) a first propagated light from the irradiated cells within a first range of angles relative to the light beam axis; (ii) a second propagated light from the irradiated cells within a second range of angles relative to the light beam axis, the second range being different than the first range; and (iii) an axial light propagated from the irradiated cells along the beam axis;

(f) wherein the system is configured to correlate a subset of DC impedance, RF conductivity, the first propagated light, the second propagated light, and the axial light measurements from the cells of the biological sample with an acute leukemic sub-type of the individual.

Prior Art Document 3 discloses a method for predicting an acute leukemia sub-type of an individual based on a biological sample obtained from blood of the individual, the method comprising: (a) delivering a hydrodynamically focused stream of the biological sample toward a cell interrogation zone of an optical element; (b) measuring, with an electrode assembly, current (DC) impedance and radiofrequency (RF) conductivity of cells of the biological sample passing individually through the cell interrogation zone; (c) irradiating, with a light beam having an axis, cells of the biological sample individually passing through the cell interrogation zone; (d) measuring, with a light detection assembly, a first propagated light from the irradiated cells within a first range of angles relative to the beam axis; (e) measuring, with the light detection assembly, a second propagated light from the irradiated cells within a second range of angles relative to the beam axis, the second range being different than the first range; (f) measuring, with the light detection assembly, axial light propagated from the irradiated cells along the beam axis; and (g) correlating a subset of DC impedance, RF conductivity, the first propagated light, the second propagated light, and the axial light measurements from the cells of the biological sample with a predicted acute leukemic sub-type of the individual.

According to the National Cancer Center, hematopoietic stem cell transplantation is performed using a therapy method of removing cancer cells and hematopoietic stem cells from patients with blood tumors, such as leukemia, myelodysplastic syndrome, malignant lymphoma, multiple myeloma, etc., by potent anticancer chemotherapy or radiation, and then transplanting new hematopoietic stem cells. Anti-cancer drugs have various adverse effects, and dangerous adverse effects thereof can cause cytopenia by destroying bone marrow cells. By the way, over time, white blood cells tend to be improved, but platelets may not survive.

In the prior art, for the treatment of leukemia, chemotherapy or radiotherapy, which is harmful to the human body, was performed, but a microwave therapy apparatus, which is less harmful to the human body than chemotherapy and radiation treatment for the treatment of leukemia, has not been researched and developed.

PRIOR ART DOCUMENTS (Patent Document 1) Korean Patent Registration No. 10-05317480000 (registered on Nov. 22, 2005; entitled "Leukemia diagnostic DNA chip", applicants: BMS Co., Ltd., IMS Co., Ltd., and Daewoong Co., Ltd.)

(Patent Document 2) Korean Patent Registration No. 10-10811140000 (registered on Nov. 1, 2011; entitled "A leukemia diagnosis apparatus using DNA information and a method of operating the same"; applicant: Inha University Industry-Academic Cooperation Foundation)

(Patent Document 3) Korean Patent Application Publication No. 10-2015-0041130 (published on Apr. 15, 2015; entitled "Leukemia classification using CPD data"; applicant: BECKMAN COULTER, INC.)

SUMMARY OF THE INVENTION

The present invention has been made in order to solve the above-described problems, and an object of the present invention is to provide a microwave therapy apparatus for blood cancer treatment wherein: i) cancer cells having a larger diameter than normal blood cells that are being circulated through a blood tube are filtered out by size filtration using a plurality of porous anodic aluminum oxide (AAO) filters and a plurality of porous glass filters provided in a dialyzer of a hemodialysis apparatus for blood cancer therapy of a leukemia patient; ii) when the diameter size of cancer cells is equal to or smaller than the size of normal blood cells, the cancer cells are caused to adhere to the nanoflower filter and are removed by radiating an RF frequency of 450 MHz through turning on/off of an RF resonator of a microwave RF generator at regular time intervals; and iii) cancer cells are removed by attraction to an RF absorber through generation of an RF frequency of 13.56 MHz, 27.12 MHz, 40.68 MHz or 54.12 MHz by the RF absorber provided on the upper side and lower side of the blood tube in an RF shield box in the hemodialyzer. The RF absorber means an RF cancer cell absorber.

Another object of the present invention is to provide a microwave therapy method for treating blood cancer.

To achieve the above object, a microwave therapy apparatus for blood cancer treatment according to Embodiment 4 comprises: a plurality of porous anodic aluminum oxide (AAO) filters or a plurality of porous glass filters provided in a dialyzer of a hemodialysis apparatus, which is connected to a blood tube; a nanoflower filter provided downstream of the plurality of porous anodic aluminum oxide (AAO) filters or the plurality of porous glass filters in the blood tube connected to an artery of a cancer patient; and an RF absorber provided downstream of the nanoflower filter and configured to attract cancer cells thereto by generating a frequency of a predetermined band, wherein blood, from which the cancer cells have been removed by the RF frequency and which includes the normal blood cells that passed through the nanoflower filter, is circulated and supplied to a blood tube connected to a vein of the blood cancer patient.

The microwave therapy apparatus for treating blood cancer further comprises a microwave RF generator configured to cause the cancer cells to adhere to the nanoflower filter and to remove the cancer cells by radiating an RF frequency through turning on/off of an RF resonator of an RF generator at regular time intervals.

The plurality of porous anodic aluminum oxide (AAO) filters allow normal blood cells having a smaller diameter than the cancer cells to pass by using a hemodialysis method, and filters abnormal blood cells including the cancer cells having a larger diameter than the normal blood cells, and when the diameter size of cancer cells is equal to or smaller than the size of the normal blood cells, the cancer cells are removed by radiating an RF frequency through turning on/off of the RF resonator of the microwave RF generator.

The plurality of porous anodic aluminum oxide (AAO) filters comprises porous anodic aluminum oxide filters containing a plurality of pores having gradually decreasing pore diameters, and three porous anodic aluminum oxide filters having different pore sizes smaller than the diameter of the cancer cells are used.

The three porous anodic aluminum oxide (AAO) filters comprise a first porous anodic aluminum oxide filter having a first pore diameter, a second porous anodic aluminum oxide filter having a second pore diameter smaller than the first pore diameter, and a third porous anodic aluminum oxide filter having a third pore diameter smaller than the second pore diameter, and the first pore diameter, the second pore diameter and the third pore diameter are hole sizes of 60, 30 and 10 μm, respectively.

The plurality of porous anodic aluminum oxide filters is separated from the dialyzer and replaced with a plurality of new porous anodic aluminum oxide filters which is harmless to the human body, after hemodialysis.

The plurality of porous glass filters comprises porous glass filters containing a plurality of pores having gradually decreasing diameters, and three porous glass filters having different pore diameters smaller than the diameter of the cancer cells are used.

The three porous glass filters comprise a first porous glass having a first pore diameter, a second porous glass filter having a second pore diameter smaller than the first pore diameter, and a third porous glass filter having a third pore diameter smaller than the second pore diameter, and the first pore diameter, the second pore diameter and the third pore diameter are hole sizes of 60, 30 and 10 μm, respectively.

The plurality of porous glass filters is separated from the dialyzer and replaced with a plurality of new porous glass filters which is harmless to the human body, after hemodialysis.

When the size of cancer cells is equal to or smaller than the size of normal blood cells, the cancer cells are adhered to the nanoflower filter, provided in the dialyzer of the hemodialysis apparatus, from the blood tube connected to the artery of the cancer patient, and the cancer cells are removed by radiating an RF frequency of 450 MHz through turning on/off of a 1.8 W microwave RF resonator at regular time intervals.

The nanoflower filter is impregnated with gold (Au) to increase reaction rate, and allows abnormal cells (i.e., cancer cells) to adhere thereto, and the nanoflower filter having the cancer cells adhered thereto is separated from the dialyzer and replaced with a new nanoflower filter, after hemodialysis of the cancer patient.

The RF absorber is provided on the upper side and lower side of the blood tube in an RF shield box in the dialyzer, the cancer cells are removed by attraction to the RF absorber through generation of an RF frequency of 13.56 MHz, 27.12 MHz, 40.68 MHz or 54.12 MHz by the RF absorber, and the RF absorber is removed after hemodialysis.

The RF absorber uses at least one frequency within a frequency range of 13.56 MHz to 54.12 MHz.

The apparatus further comprises an RF shield box (RF shield room) configured to shield the blood tube 10 in the dialyzer of the hemodialysis apparatus. The RF shield box is made of a plastic, aluminum, ceramic or rubber material, and shields frequencies outside the hemodialyzer using the RF shield material. The RF shield box is provided in the form of a rectangular box shape, a cylindrical shape, a polygonal shape such as a pentahedral, hexahedral, heptahedral or octahedral shape, in the dialyzer of the hemodialysis apparatus.

The RF shield material shields an RF frequency in the MHz to GHz band.

The RF shield material comprises silver (Ag) as a screening material. Also, it comprises an Aaronia shield material that shields an RF frequency in a band of 100 MHz to 10 GHz, or Aaronia X-steel that comprises stainless steel as a screening material and shields an RF frequency in a band of 1 MHz to 50 GHz. After hemodialysis, the RF absorber is removed.

To achieve another object of the present invention, a microwave therapy method for treating blood cancer comprises steps of: (a) providing a plurality of porous anodic aluminum oxide (AAO) filters or a plurality of porous glass filters in a dialyzer of a hemodialysis apparatus, to which blood is supplied from a blood tube connected to the artery of a leukemia patient when blood is circulated in the blood flow direction by operation of a blood pump during hemodialysis, allowing normal blood cells having a smaller diameter than cancer cells to pass through the filters, and filtering, by the filters, abnormal blood cells including cancer cells having a larger diameter than the normal blood cells; (b) providing a nanoflower filter downstream of the plurality of AAO filters or the plurality of porous glass filters provided in the dialyzer of the hemolysis apparatus, and allowing the cancer cells to adhere to the nanoflower filter; (c) removing the cancer cells by radiating an RF frequency through turning on/off of an RF resonator of a microwave RF generator at regular intervals; and (d) attracting the cancer cells to an RF absorber, provided downstream of the nanoflower, by generation of a frequency of a predetermined band by the RF absorber, and removing the RF absorber, wherein the blood, from which the cancer cells have been removed and which includes the normal blood cells, is circulated and supplied to a blood tube connected to the vein of the body of the cancer patient in the blood flow direction.

When the size of cancer cells is equal to or smaller than the size of normal blood cells, the method further comprises a step of removing the cancer cells in the filters provided in the dialyzer of the hemolysis apparatus, from the blood tube connected to the artery of the cancer patient, by radiating an RF frequency through turning on/off of an RF resonator of a 1.8 W RF microwave RF generator at regular time intervals.

The RF absorber is provided on the upper side and lower side of the blood tube in an RF shield box in the hemodialyzer, and the method further comprises removing the cancer cells by attraction to the RF absorber through generation of an RF frequency of 13.56 MHz, 27.12 MHz, 40.68 MHz, or 54.12 MHz, by the RF absorber, and removing the RF absorber after hemodialysis.

In addition, the RF absorber uses at least one frequency within a frequency range of 13.56 MHz to 54.12 MHz.

The method further comprises a step of removing the plurality of porous anodic aluminum oxide (AAO) filters or the plurality of porous glass filters, the nanoflower filters having the cancer cells adhered thereto, and the RF absorber having the cancer cells attracted thereto, after hemodialysis.

Advantageous Effects

The microwave therapy apparatus and method for blood cancer treatment according to the present invention have the following effects: i) cancer cells having a larger diameter than normal blood cells that are being circulated through the blood tube are filtered out by size filtration using the plurality of porous anodic aluminum oxide (AAO) filters and the plurality of porous glass filters provided in the dialyzer of the hemodialysis apparatus for blood cancer therapy of a leukemia patient; ii) when the diameter size of cancer cells is equal to or smaller than the size of normal blood cells, the cancer cells are caused to adhere to the nanoflower filter and are removed by radiating an RF frequency of 450 MHz through turning on/off of the RF resonator of the microwave RF generator at regular time intervals; and iii) cancer cells are removed by attraction to the RF absorber through generation of an RF frequency of 13.56 MHz, 27.12 MHz, 40.68 MHz or 54.12 MHz by the RF absorber provided on the upper side and lower side of the blood tube in the RF shield box in the hemodialyzer.

The blood, from which the abnormal blood cells have been filtered out by hemodialysis, is circulated and supplied to the vein of the body of the leukemia patient in the blood flow direction (artery—vein), and the cancer cells are removed after hemodialysis of the leukemia patient.

The microwave therapy apparatus for leukemia treatment according to the present invention, which is less harmful to the human body, is less harmful to the human body than existing chemotherapy and radiotherapy, and may be used to treat blood cancer, such as leukemia, and cancer, by removing cancer cells.

BRIEF DESCRIPTION OF THE DRAWINGS

The above and other aspects, features and advantages of certain exemplary embodiments of the present invention will be more apparent from the following detailed description taken in conjunction with the accompanying drawings, in which.

DETAILED DESCRIPTION OF THE INVENTION

Hereinafter, the preferred embodiments, configuration and operation of the present invention will be described in detail with reference to the accompanying drawings.

Figure 1:
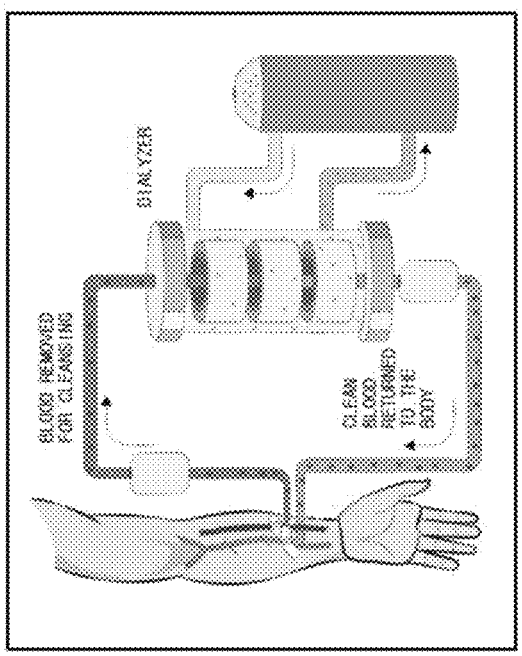
FIG. 1 shows blood cells having different pore sizes, including cancer cells (abnormal cells) having a relatively larger diameter than normal blood cells.
Figure 1:
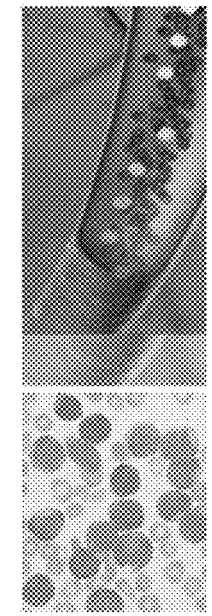
Figure 1:
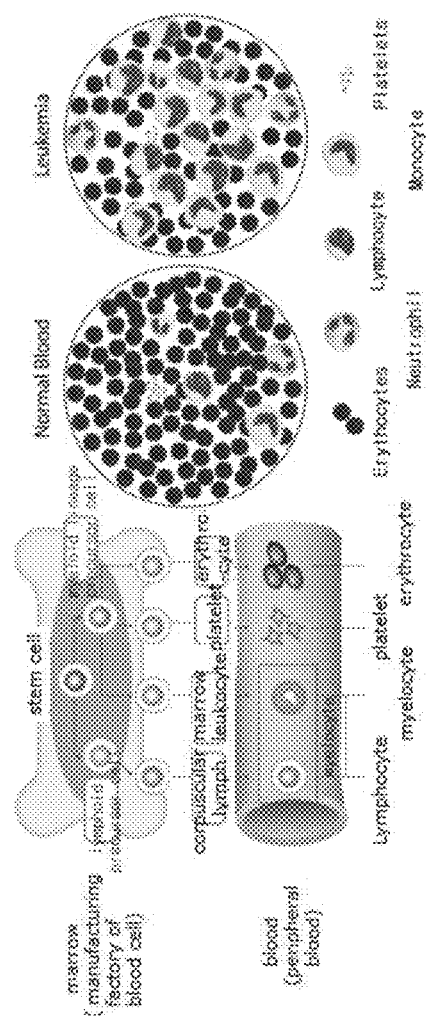
Figure 1:
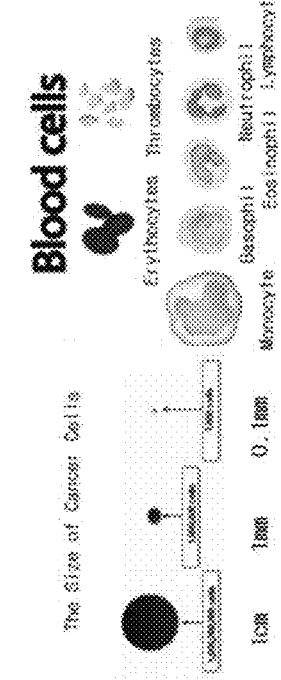
Figure 1:
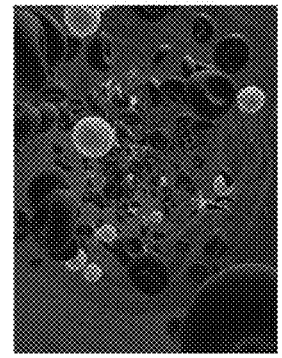

FIG. 1 shows blood cells having different pore sizes, including cancer cells (abnormal cells) having a relatively larger diameter than normal blood cells. The bones of our body maintain the shape of the body and are involved in calcium regulation, and inside the bones, bone marrow tissues that are less dense than the bones make blood cells, such as white blood cells, red blood cells, and platelets.

Leukemia is a blood cancer (bone marrow cancer) that occurs in white blood cells among these blood cells, and the production of normal white blood cells, red blood cells, and platelets is suppressed by excessively proliferation of abnormal white blood cells (leukemia cells). A decrease in the number of normal white blood cells can cause a decline in immunity and cause sepsis caused by bacterial infection, and a decrease in the number of red blood cells causes anemia symptoms (dizziness, headache, and difficulty in breathing), and a decrease in the number of platelets causes a tendency to bleed.

When leukemia occurs, white blood cells increase, and cancer cells become larger in size. Using a hemodialysis method, cancer cells having a larger diameter than normal blood cells that are being supplied through a blood tube in the blood flow direction are removed by size filtration using a plurality of AAO filters (Embodiment 1) or a plurality of porous glass filters (Embodiment 2) in a dialyzer of a hemodialysis apparatus.

Figure 2:
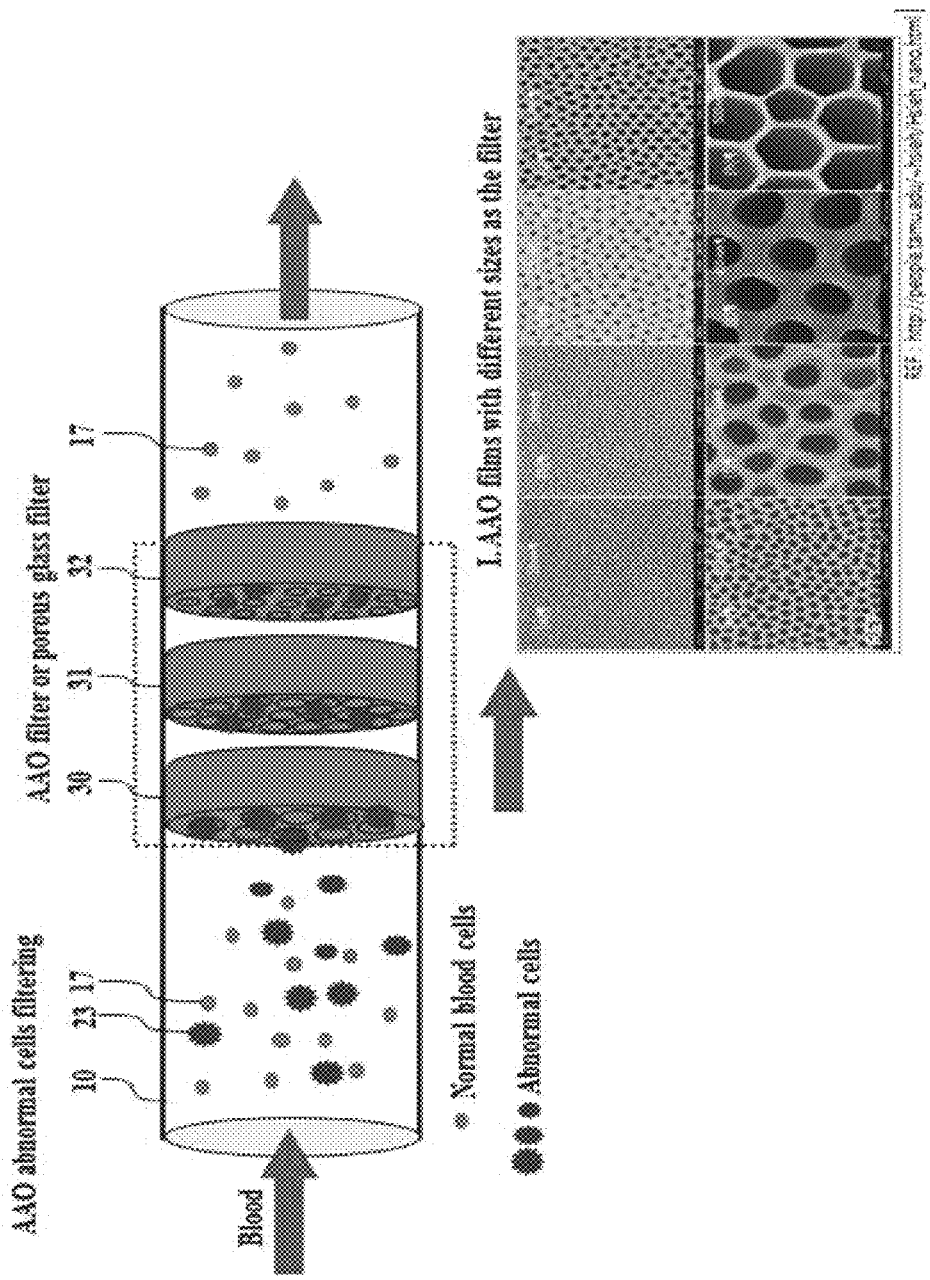
FIG. 2 shows a microwave therapy apparatus for leukemia treatment according to embodiments of the present invention, which comprise a plurality of porous anodic aluminum oxide (AAO) filters (Embodiment 1) or a plurality of porous glass filters (Embodiment 2).

FIG. 2 shows a microwave therapy apparatus for leukemia treatment according to embodiments of the present invention, which comprise a plurality of porous anodic aluminum oxide (AAO) filters (Embodiment 1) or a plurality of porous glass filters (Embodiment 2).

Figure 3:
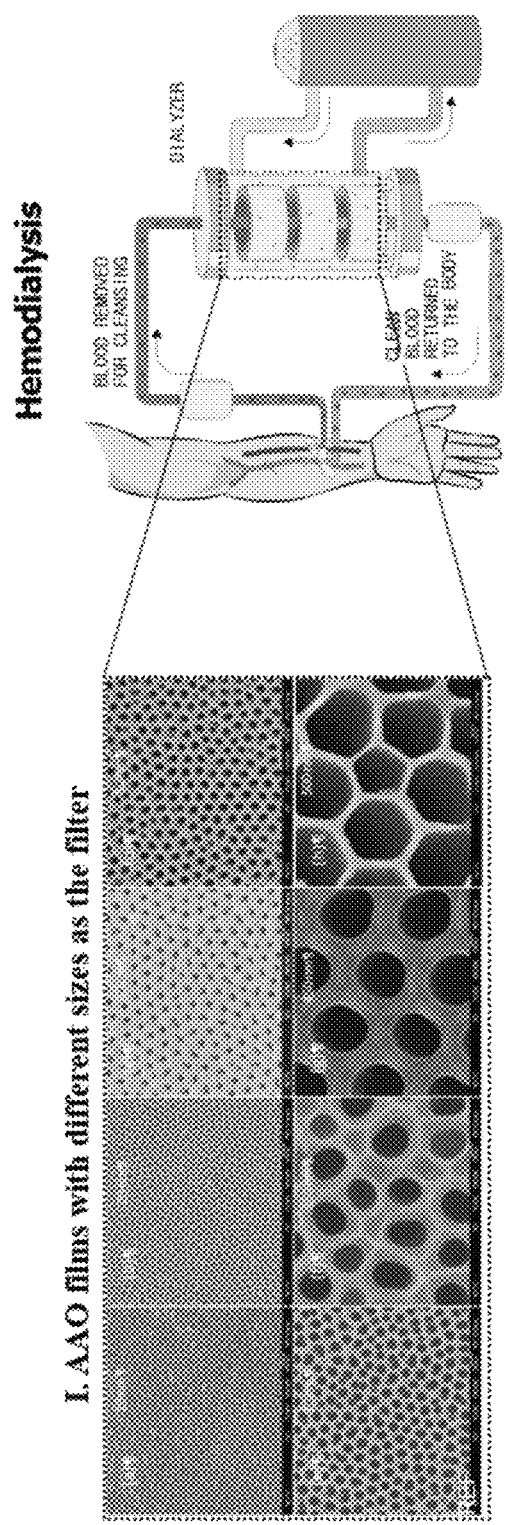
FIG. 3 shows a hemodialysis method for leukemia treatment according to the present invention, which is performed using three porous anodic aluminum oxide (AAO) filters provided in a dialyzer.

FIG. 3 shows a hemodialysis method for leukemia treatment according to the present invention, which is performed using three porous anodic aluminum oxide (AAO) filters provided in a dialyzer.

The present invention relates to a microwave therapy apparatus and method for treating blood cancer, and more particularly, to a microwave therapy apparatus and method wherein: i) cancer cells having a larger diameter than normal blood cells that are being circulated through a blood tube are filtered out by size filtration using a plurality of porous anodic aluminum oxide (AAO) filters and a plurality of porous glass filters provided in a dialyzer of a hemodialysis apparatus for blood cancer therapy of a leukemia patient; ii) when the diameter size of cancer cells is equal to or smaller than the size of normal blood cells, the cancer cells are caused to adhere to the nanoflower filter and are removed by radiating an RF frequency of 450 MHz through turning on/off of an RF resonator of a microwave RF generator at regular intervals; and iii) cancer cells are removed by attraction to an RF absorber through generation of an RF frequency of 13.56 MHz, 27.12 MHz, 40.68 MHz or 54.12 MHz by the RF absorber provided on the upper side and lower side of the blood tube in an RF shield box in the hemodialyzer.

The blood, from which the abnormal blood cells have been filtered out by hemodialysis, is circulated and supplied to the vein of the body of the leukemia patient in the blood flow direction (artery—vein), and the cancer cells are removed after hemodialysis of the leukemia patient.

(Embodiment 1) Use of AAO Filter

A microwave therapy apparatus using a porous anodic aluminum oxide (AAO) filter for leukemia treatment comprises: a plurality (three) of porous anodic aluminum oxide (AAO) filters 30, 31 and 32 to which blood is supplied from a blood tube 10 connected to the artery of a leukemia patient and which have a smaller diameter than cancer cells provided in a blood pump and a dialyzer of a hemodialysis apparatus and have a gradually decreasing pore diameter. The plurality of porous anodic aluminum oxide (AAO) filters 30, 31 and 32 or porous glass filters is provided in the dialyzer of the hemodialysis apparatus, allow normal blood cells 17 having a smaller diameter than cancer cells to pass on the basis of a hemodialysis method, and filters abnormal blood cells 23 including cancer cells having a larger diameter than the normal blood cells. When the diameter of the cancer cells is equal to or smaller than the diameter of the normal blood cells, the cancer cells are removed by radiating a 450 MHz RF frequency through turning on/off of an RF resonator of a 1.8 W microwave RF generator at regular time intervals and, and the blood, from which the abnormal blood cells 23 have been removed and includes which the normal blood cells 17, is circulated and supplied through the blood tube 10 to the blood tube 10 connected to the vein of the body of the leukemia patient in the blood flow direction (artery—vein).

The plurality of porous anodic aluminum oxide (AAO) filters 30, 31 and 32 comprise porous anodic aluminum oxide filters containing a plurality of pores whose diameter is smaller than the diameter of cancer cells and decreases gradually, and three porous anodic aluminum oxide filters having different pore diameters smaller than the diameter of cancer cells are used.

The three porous anodic aluminum oxide (AAO) filters 30, 31 and 32 include a first porous anodic aluminum oxide filter 30 having a first pore diameter, a second porous anodic aluminum oxide filter 31 having a second pore diameter smaller than the first pore diameter, and a third porous anodic aluminum oxide filter 32 having a third pore diameter smaller than the second pore diameter, and the first pore diameter, the second pore diameter and the third pore diameter are gradually decreasing diameters corresponding to hole sizes of 60 μm, 30 μm and 10 μm, respectively.

In addition, a microwave therapy method for leukemia treatment using a porous anodic aluminum oxide filter according to the present invention is a microwave therapy method for treating blood cancer, such as leukemia, which uses a plurality of anodic aluminum oxide (AAO) filters provided in a dialyzer of a hemodialysis apparatus, the method comprising steps of:

(a) allowing normal blood cells 17 which have a smaller diameter than cancer cells, to pass through a plurality of porous anodic aluminum oxide (AAO) filters 30, 31 and 32 provided in a dialyzer of a hemodialysis apparatus to which blood is supplied from a blood tube 10 connected to the arterial blood vessel of a leukemia patient, during circulation of the blood by operation of a blood pump, and capturing abnormal blood cells, including cancer cells 23 having a larger diameter than the normal cells 17, by the AAO filters 30, 31 and 32, and when the diameter of the cancer cells is equal to or smaller than the size of the normal blood cells, the cancer cells are removed by radiating a radio-frequency through turning on/off of a microwave RF generator at regular time intervals; and (b) circulating and supplying the blood, from which the abnormal blood cells 23 have been removed and which includes the normal blood cells 17, through the blood tube 10 to a blood tube connected to the vein of the body of the leukemia patient in the blood flow direction.

The plurality of porous anodic aluminum oxide (AAO) filters 30, 31 and 32 comprise porous anodic aluminum oxide filters containing a plurality of pores having gradually decreasing diameters smaller than the diameter of cancer cells, and for example, three porous anodic aluminum oxide filters having different pore diameters smaller than the diameter of cancer cells are used.

The three porous anodic aluminum oxide (AAO) filters 30, 31 and 32 include a first anodic aluminum oxide filter 30 having a first pore diameter, a second porous anodic aluminum oxide filter 31 having a second pore diameter smaller than the first pore diameter, and a third porous anodic aluminum oxide filter 32 having a third pore diameter smaller than the second pore diameter, and the first pore diameter, the second pore diameter and the third pore diameter are gradually decreasing diameters corresponding to hole sizes of 60 μm, 30 μm and 10 μm, respectively.

When the size of cancer cells is equal to or smaller than the size of normal blood cells, the cancer cells are removed in the filters provided in the dialyzers, from the blood tube connected to the artery of the cancer patient, by radiating an RF frequency of 450 MHz through turning on/off of a 1.8 W microwave RF generator at regular time intervals.

The method further comprises, after hemodialysis, step (c) of separating the plurality of porous anodic aluminum oxide filters or the plurality of porous glass filters from the dialyzer, followed by replacement with a plurality of fresh porous anodic aluminum oxide filters which is harmless to the human body.

After hemodialysis, the porous anodic aluminum oxide filters or the plurality of porous glass filters is separated from the dialyzer and replaced with a plurality of fresh porous anodic aluminum oxide filters which is harmless to the human body.

Figure 4:
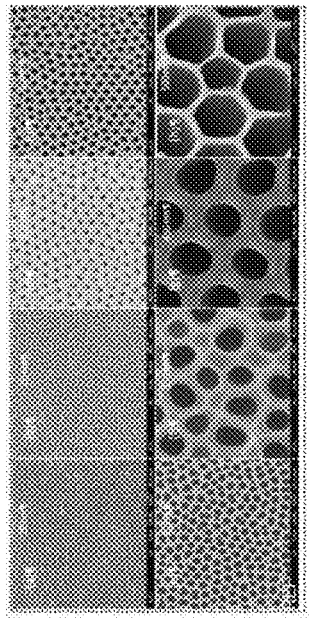
FIG. 4 shows that the pore size of a porous anodic aluminum oxide (AAO) filter, which is chemically stable and harmless to the human body, can be adjusted on abnormal cells (cancer cells).

FIG. 4 shows that the pore size of a porous anodic aluminum oxide (AAO) filter, which is chemically stable and harmless to the human body, can be adjusted on abnormal cells (cancer cells).

Embodiment 2 describes the case in which a plurality of glass filters is used instead of a plurality of AAO filters provided in a dialyzer of a hemodialysis apparatus comprising a blood tube and a blood pump (Embodiment 1).

(Embodiment 2) Microwave Therapy Apparatus for Treating Blood Cancer Using Plurality of Porous Glass Filters Provided in Dialyzer A microwave therapy apparatus for treating blood cancer such as leukemia according to Embodiment 2 comprises a plurality (three) of porous glass filters in a dialyzer of a hemodialysis apparatus, to which blood is supplied from a blood tube connected to the artery of a leukemia patient, wherein the plurality of porous glass filters is provided in the dialyzer of the hemodialysis apparatus, allows normal blood cells having a smaller pore diameter than cancer cells to pass on the basis of a hemodialysis method, and filters abnormal blood cells including cancer cells having a larger pore diameter than the normal blood cells. When the diameter of cancer cells is equal to or smaller than the size of normal blood cells, the cancer cells are removed by radiating a 450 MHz RF frequency through turning on/off of an RF resonator of a 1.8 W microwave RF regenerator at regular time intervals.

The blood, from which the abnormal blood cells have been removed and includes the normal blood cells, is circulated and supplied to a blood tube connected to the vein of the body of the leukemia patient in the blood flow direction.

The plurality of porous glass filters 30, 31 and 32 comprises porous glass filters containing a plurality of pores whose diameter is smaller than the diameter of cancer cells and decreases gradually, and three porous glass filters having different pore diameters smaller than the diameter of cancer cells are used.

The three porous glass filters 30, 31 and 32 include a first porous glass filter 30 having a first pore diameter, a second porous glass filter 31 having a second pore diameter smaller than the first pore diameter, and a third porous glass filter 32 having a third pore diameter smaller than the second pore diameter, and the first pore diameter, the second pore diameter and the third pore diameter are gradually decreasing diameters corresponding to hole sizes of 60 μm, 30 μm and 10 μm, respectively.

When the size of cancer cells is equal to or smaller than the size of normal blood cells, the cancer cells are removed in the filters provided in the dialyzers, from the blood tube connected to the artery of the cancer patient, by radiating an RF frequency of 450 MHz through turning on/off of a 1.8 W microwave RF generator at regular time intervals.

After hemodialysis, the plurality of porous glass filters 30, 31 and 32 is separated from the dialyzer and replaced with a plurality of fresh porous glass filters which is harmless to the human body.

The microwave therapy apparatus for treating blood cancer such as leukemia according to the present invention is less harmful to the human body than existing chemotherapy or radiotherapy, may be applied for leukemia treatment and cancer treatment, and will be applied to medical clinical trials.

Figure 5:
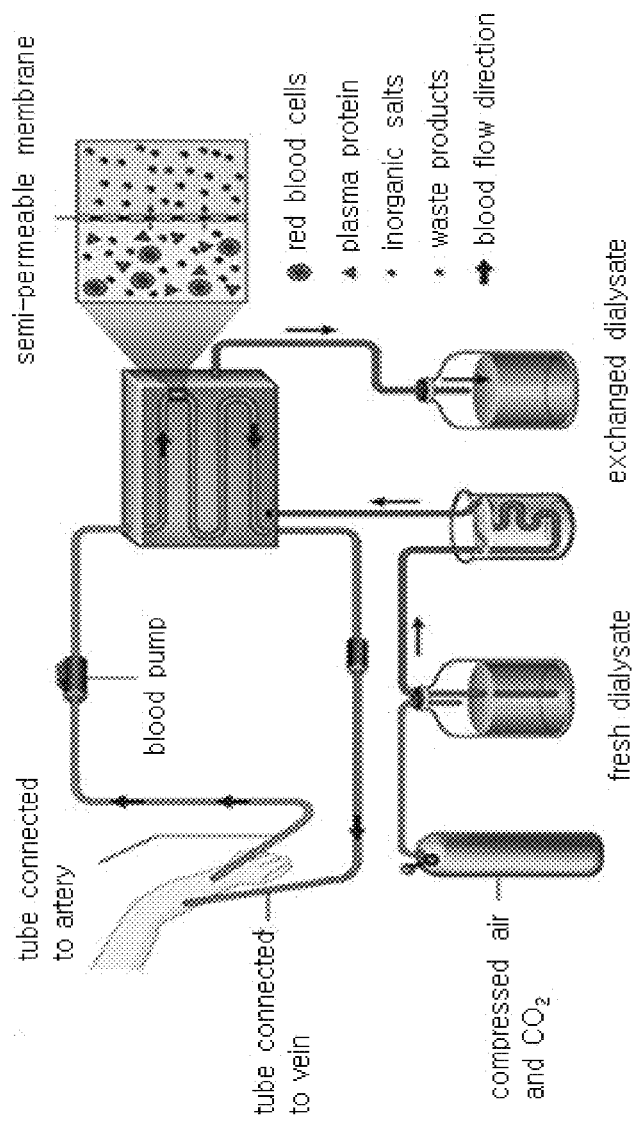
FIG. 5 shows a hemodialysis apparatus comprising a blood tube, a blood pump and a dialyzer.

FIG. 5 shows a hemodialysis apparatus comprising a blood tube, a blood pump and a dialyzer. In an embodiment, the dialyzer includes three porous anodic aluminum oxide (AAO) filters having pore diameters of 60, 30 and 10 μm, respectively.

For reference, hemodialysis is a method in which patient's blood is filtered by passage through a dialyzer (artificial kidney) and then introduced again into the patient's blood vessel. It is a dialysis treatment that is applied to terminal renal failure patients. It performs a major function for the kidneys by removing nitrogen-containing waste products, generated by excessive water and protein metabolism, from the patient's blood, placing a tube made of a dialysis membrane in a solution configured to improve the plasma acid/base equilibrium and the electrolyte concentration, and circulating a portion of the patient's blood in this tube. The apparatus for performing this hemodialysis is called a dialyzer (artificial kidney). The kidneys are present on the left and right sides of the body, respectively, and function to filter out waste products in the blood into the urine and control the concentration of electrolytes in the blood or control blood pressure.

For hemodialysis, it is needed to provide, on the vein side, a place through which arterial blood is drawn from the patient and connected to the artificial kidney circuit and the dialyzed blood is returned back to the patient, in order to make a passage for dialysis treatment in the blood vessel. This blood access is called a shunt, and methods for blood access include three methods: an outer shunt method using a scrivener shunt in which a cannula made of plastic is inserted in an artery and vein; an inner shunt method in which body fluids are extracted by inputting a hollow, fine needle whenever dialysis is performed on a vein enlarged by anastomosing the artery and vein; and an artificial blood vessel implantation method. In particular, in the case of the inner shunt method, arteries and venous blood vessels are connected through surgery to make the blood vessels thicker, which makes dialysis possible. Here, the thickened blood vessel is called an arteriovenous fistula. When the arteriovenous fistula is thickened by surgery, dialysis treatment begins a needle is inserted and connected to a dialyzer. The inner shunt method is method is a technique that is widely used recently. There are three types of dialyzers: coil type, flat plate type, and hollow fiber type. The hollow fiber type is most frequently used. In addition, heparin is used to prevent blood from clotting inside the dialyzer. Hemodialysis is usually performed 3 times a week for 3 to 5 hours each time.

(Embodiment 3) Microwave Therapy Apparatus and Method Using Nanoflowers

Figure 6:
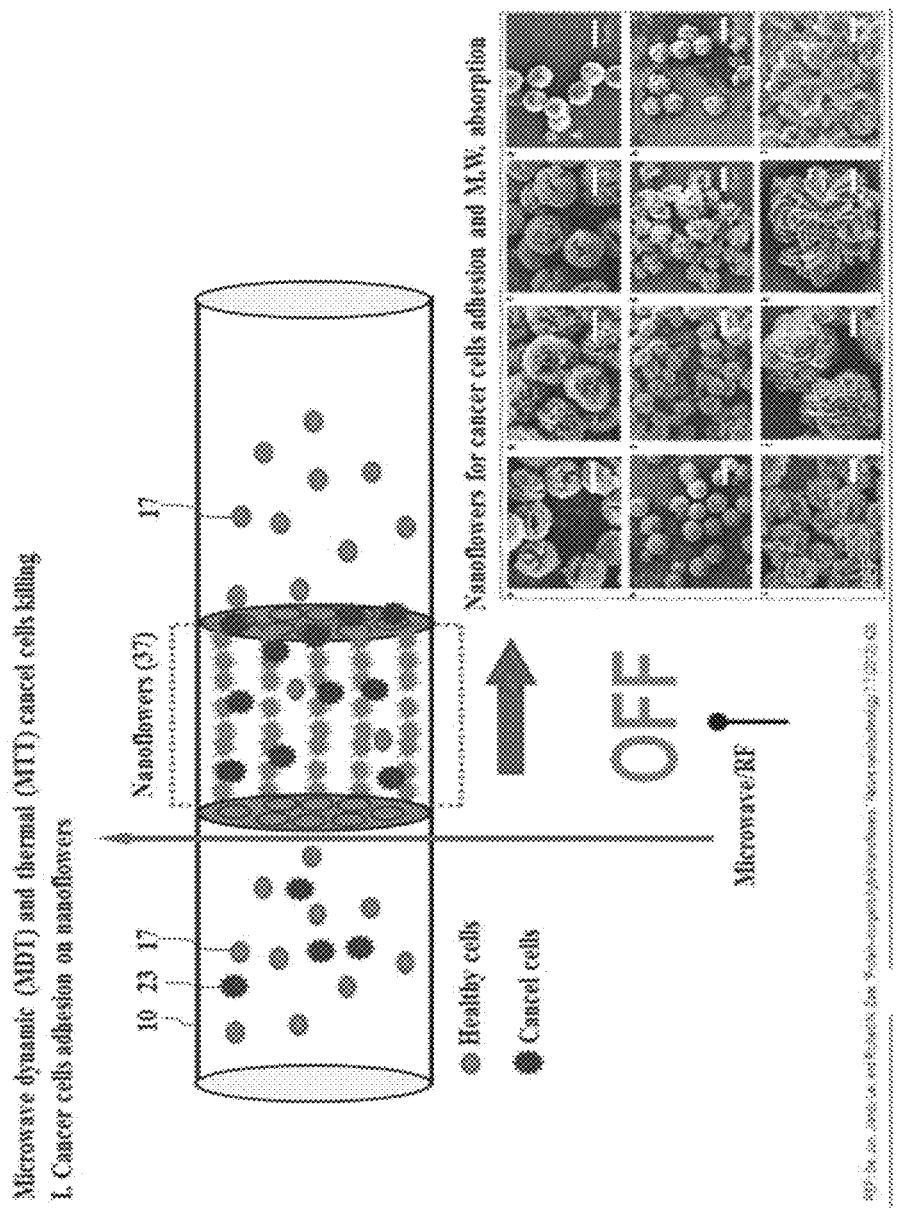
FIGS. 6 to 8 show a microwave therapy method for cancer treatment according to Embodiment 3 of the present invention, which is performed by using nanoflowers that remove cancer cells using an RF frequency.
Figure 7:
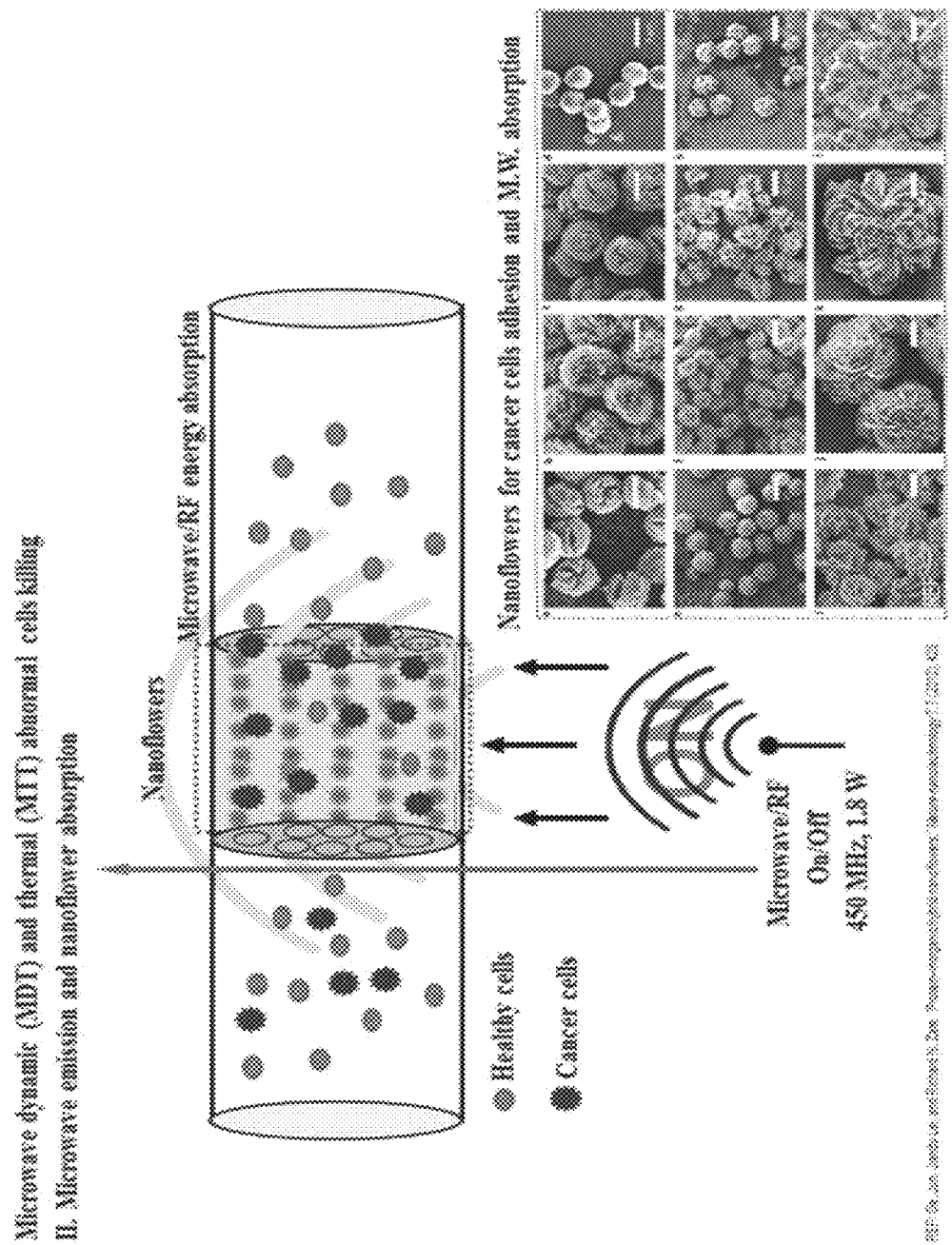
Figure 8:
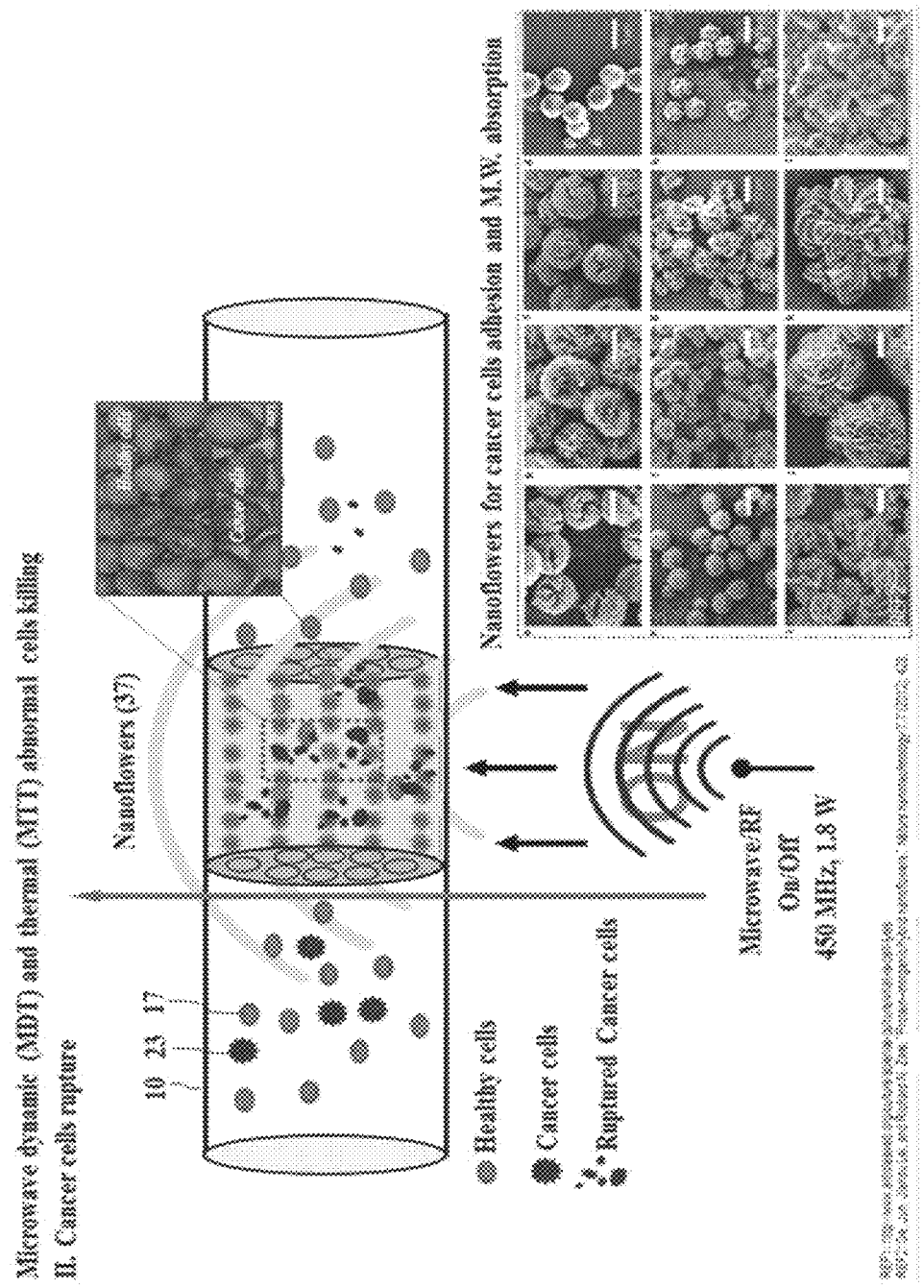
Figure 9:
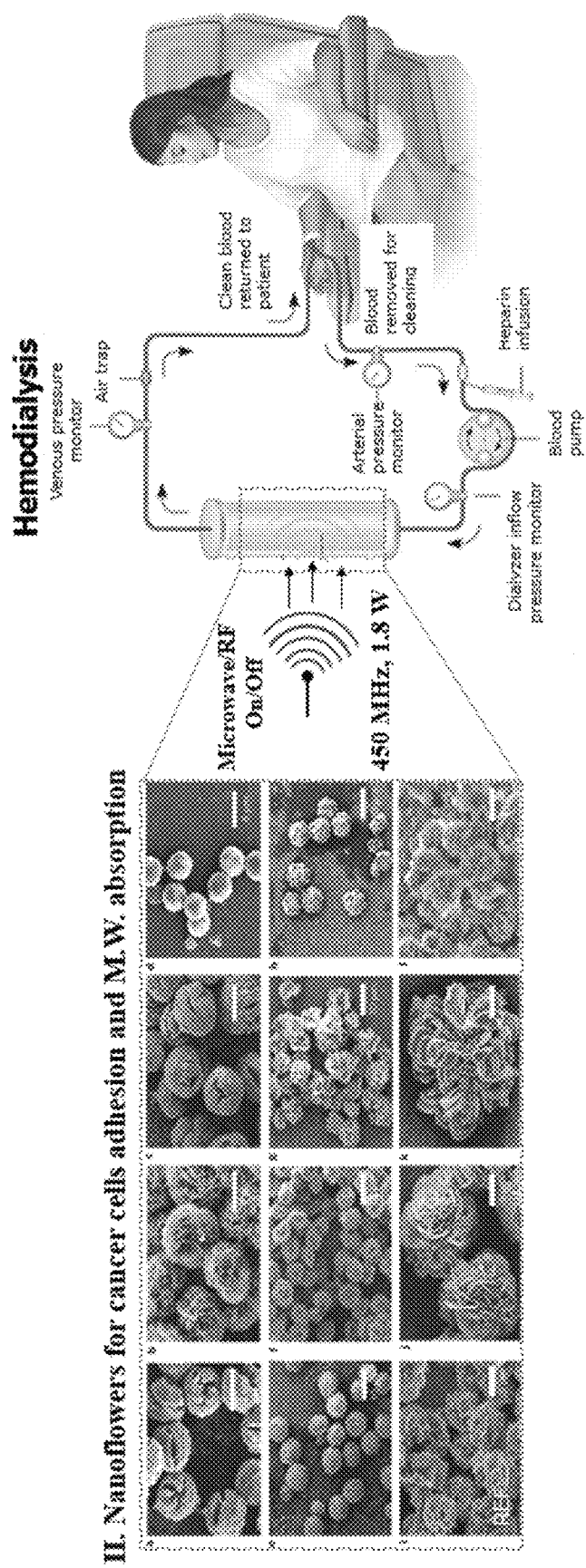
FIG. 9 shows removing cancer cells by using a first-stage AAO filter and a second-stage nanoflower filter.

FIGS. 6 to 8 show a microwave therapy apparatus and method using nanoflowers for cancer treatment, which remove cancer cells by using an RF frequency, according to Embodiment 3 of the present invention.

Figure 10:
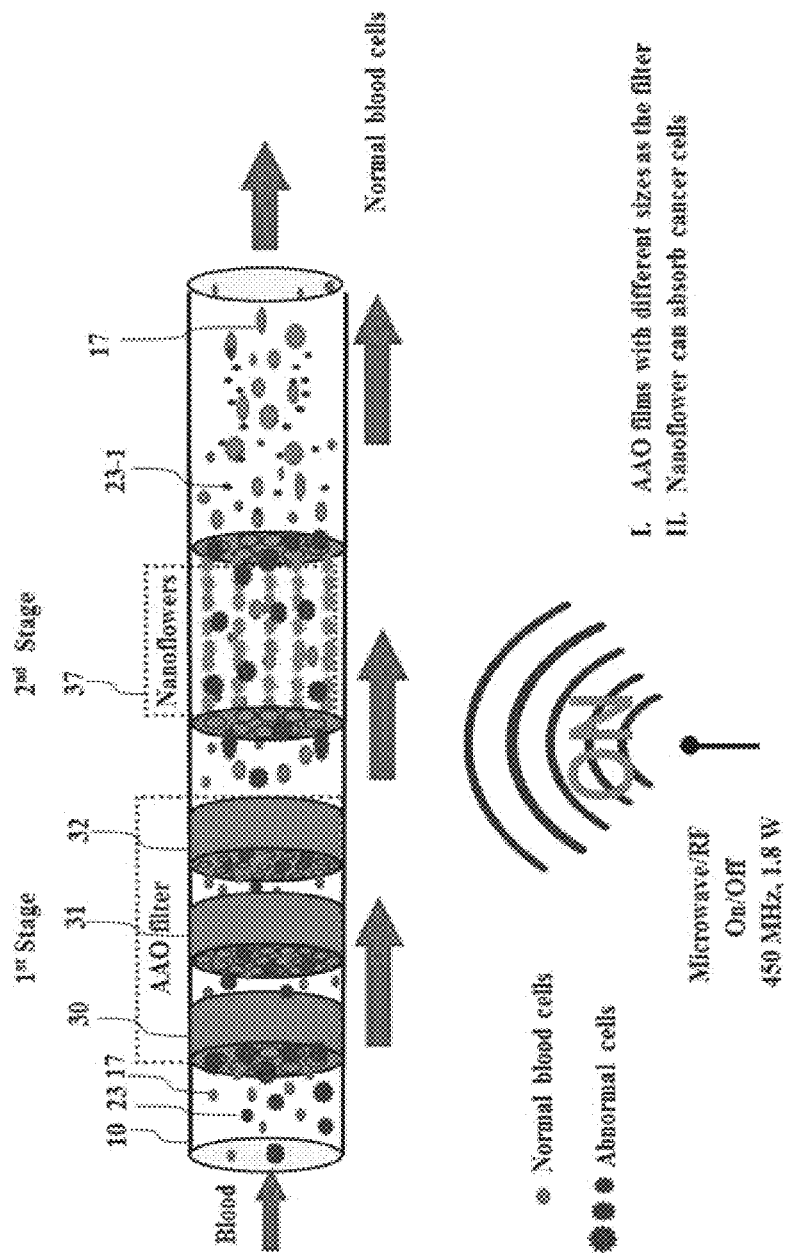
FIG. 10 shows removing cancer cells in a nanoflower filter of a hemodialysis apparatus by radiating an RF frequency of 450 MHz through turning on/off of a 1.8 W microwave RF resonator, and shows removing cancer cells by using a first-stage AAO filter and a second-stage nanoflower filter in a dialyzer.

FIG. 10 shows that cancer cells are removed by radiating a 450 MHz RF frequency through turning on/off of a 1.8 W microwave RF resonator at regular time intervals in a nanoflower filter provided in a dialyzer of a hemodialysis apparatus.

Referring to FIGS. 6 and 7, a microwave therapy apparatus using nanoflowers for cancer treatment according to the present invention is a hemodialysis apparatus comprising a blood tube, a blood pump and a dialyzer, which is used when cancer cells 23 are not filtered out according to size because the size thereof is equal to or smaller than the size of normal blood cells 17, the apparatus comprising a nanoflower filter 37 in the dialyzer of the hemodialysis apparatus, to which blood is supplied from the blood tube 10 connected to the artery of the cancer patient when the blood is circulated in the blood flow direction by operation of the blood pump during hemodialysis. In the apparatus, the cancer cells are adhered to the nanoflower filter 37, the cancer cells are removed by radiating a 450 MHz RF frequency turning on/off of a 1.8 W microwave RF resonator at regular time intervals, and the blood 17 including the normal blood cells, from which the cancer cells have been removed by the 450 MHz RF frequency, is circulated and supplied to a blood tube connected to the vein of the body of the cancer patient in the blood flow direction (artery—vein), thereby removing the cancer cells by the nanoflower filter 37 and the RF frequency after hemodialysis of the cancer patient.

Referring to FIG. 8, the microwave therapy apparatus for blood cancer treatment using the nanoflower filter 37 provided in the dialyzer comprises the nanoflower filter 37 in the dialyzer of the hemodialysis apparatus, to which blood is supplied from the blood tube connected to the artery of the cancer patient. The apparatus allows the cancer cells to adhere to the nanoflower filter, removes the cancer cells by radiating the RF frequency through turning on/off of the RF resonator of the microwave RF generator at regular time intervals, and circulates and supplies the blood, from which the cancer cells have been removed by the RF frequency and which includes the normal blood cells that passed through the nanoflower filter, to the blood tube connected to the vein of the body of the cancer patient in the blood flow direction (artery—vein).

If the size of the cancer cells is equal to or smaller than the size of the normal blood cells, the apparatus, when supplied from the blood tube connected to the artery of the cancer patient, removes the cancer cells in the nanoflower filter 37 provided in the dialyzer of the hemodialysis apparatus by radiating a 450 MHz RF frequency through turning on/off of the RF resonator of the 1.8 W microwave RF generator at regular time intervals.

The microwave RF frequency ruptures or kills abnormal cells by microwave dynamic therapy (MDT) and microwave thermal therapy (MTT).

Microwave dynamic therapy (MDT) removes cancer cells by radiating a 450 MHz RF frequency by using an RF resonator of a 1.8 W microwave RF generator at regular time intervals. In addition, according to microwave e thermal therapy (MTT), cancer cells can be killed by heat at 41° C. to 47° C. For example, cancer cells can be killed at 42.3° C. by heat at 41° C. or higher, and normal blood cells survive at 48° C.

The nanoflower filter is impregnated with gold (Au) to increase reaction rate, and allows abnormal cells (i.e., cancer cells) to adhere thereto.

To the nanoflowers, cancer cells killed by radiating the RF frequency adhere.

For reference, in chemistry, "nanoflower" refers to a compound of a certain element that resembles a flower when viewed under a microscope or, in some cases, forms a tree called nanobouquets or nanotrees. Since this structure is nanometers in length and thick, it can be observed only with an electron microscope (SEM or TEM).

The nanoflower filter (37) is impregnated with gold (Au) in order to increase the reaction rate, and is made of a material to which abnormal cells (i.e., cancer cells) adhere.

Specifically, protein-inorganic hybrid nanoflowers are used. For example, nanoparticles fabricated by coating a protein on an inorganic material, such as Mn, Fe or Se, which is harmless to the blood of the human body, are used.

There are several types of receptors, proteins, lipids and polysaccharides on the membrane of cancer cells, and there are several types of substances that have affinity for them, and thus they are used together when making nanoflowers. They are also harmless to the human body because they are present in the human body. The nanoflowers 37 are impregnated with gold (Au) in order to increase the reaction rate. Some researchers previously made Fe or Se nanoflowers, and will attempt to make Mn nanoflowers.

Nanoflowers show a structure similar to flowers, and are a group of newly developed nanoparticles that are attracting much attention due to their high stability and high efficiency of petal.

Nanoflowers can be used as biosensors to quickly and accurately detect conditions such as diabetes, Parkinson's disease, Alzheimer's disease, and food infections. According to a recent study, the use of Raman spectroscopy can observe three-dimensional nano-filters for improving surface sensitivity. The nanoflower system has a high surface volume ratio and high adsorption efficiency.

After hemodialysis of the cancer patient by the above-described apparatus, the nanoflower filter to which cancer cells adhered is separated from the dialyzer and replaced with a new nanoflower filter.

A microwave therapy method using nanoflowers provided in a dialyzer of a hemodialysis apparatus according to the present invention comprises steps of: (a) providing a nanoflower filter in a dialyzer of a hemodialysis apparatus, to which blood is supplied from a blood tube connected to the artery of a cancer patient when the blood is circulated in the blood flow direction by operation of a blood pump, and removing cancer cells in the nanoflower filter by radiating an RF frequency through turning on/off of a microwave RF resonator at regular time intervals; and (b) circulating and supplying the blood, from which the cancer cells have been removed by the RF frequency and which includes the normal blood cells that passed through the nanoflower filter, to the blood tube connected to the vein of the body of the cancer patient in the blood flow direction.

In the method, if the size of cancer cells is equal to or smaller than the size of normal blood cells, the cancer cells are removed in the nanoflower filter, provided in the analyzer of the hemodialysis apparatus, from the blood tube connected to the artery of the cancer patient, by radiating a 450 MHz RF frequency through turning on/off of a 1.8 W microwave RF resonator at regular time intervals. The nanoflower filter is impregnated with gold (Au) to increase the reaction rate, and abnormal cells (i.e., cancer cells) adhere thereto.

The method further comprises step (c) of replacing the nanoflower filter, to which the cancer cells adhered to the nanoflower filter in the dialyzer, with a fresh nanoflower filter, after hemodialysis of the cancer patient.

FIG. 10 shows removing cancer cells using a first-stage AAO filter and a second-stage nanoflower filter in a dialyzer.

In addition, a microwave therapy apparatus for treating blood cancer according to the present invention comprises: a plurality of porous anodic aluminum oxide (AAO) filters or a plurality of porous glass filters provided in a dialyzer of a hemodialysis apparatus, which is connected to a blood tube to which blood is supplied; and a nanoflower filter which is provided downstream of the plurality of porous anodic aluminum oxide (AAO) filters or the plurality of porous glass filters and to which cancer cells adhere when blood is supplied from a blood tube connected to the artery of the cancer patient. In the apparatus, the cancer cells are removed by radiating an RF frequency through switching on/off of a microwave RF generator at regulator time intervals, and the blood, from which the cancer cells have been removed by the RF frequency and includes normal blood cells that passed through the nanoflower filter, is circulated and supplied to a blood tube connected to the vein of the blood cancer patient in the blood flow direction.

Using a hemodialysis method, the plurality of porous anodic aluminum oxide (AAO) filter allows passage of normal blood cells 17 having a smaller pore diameter than cancer cells, and captures normal blood cells including cancer cells 23 having a larger pore diameter than the normal blood cells 17. If the diameter size of cancer cells is equal to or smaller than normal blood cells, the cancer cells (23-1) are removed by radiating an RF frequency through turning on/off of an RF resonator of a microwave RF generator at regular time intervals.

If the size of cancer cells is equal to or smaller than the size of normal blood cells, the microwave therapy apparatus for treating blood cancer allows the cancer cells to adhere to the nanoflower filter, provided in the dialyzer, from the blood tube connected to the artery of the cancer patient, and removes the cancer cells by radiating a 450 MHz RF frequency through turning on/off of a 1.8 W microwave RF resonator at regular time intervals.

The nanoflower filter 37 is impregnated with gold (Au) to increase reaction rate, and allows abnormal cells (i.e., cancer cells to adhere thereto. After hemodialysis of the cancer patient, the nanoflower filter to which the cancer cells adhered is separated from the dialyzer and replaced with a new (fresh) nanoflower filter.

Embodiment 4

Plurality of porous AAO filters or porous glass filters/nanoflowers/RF absorber

Figure 11:
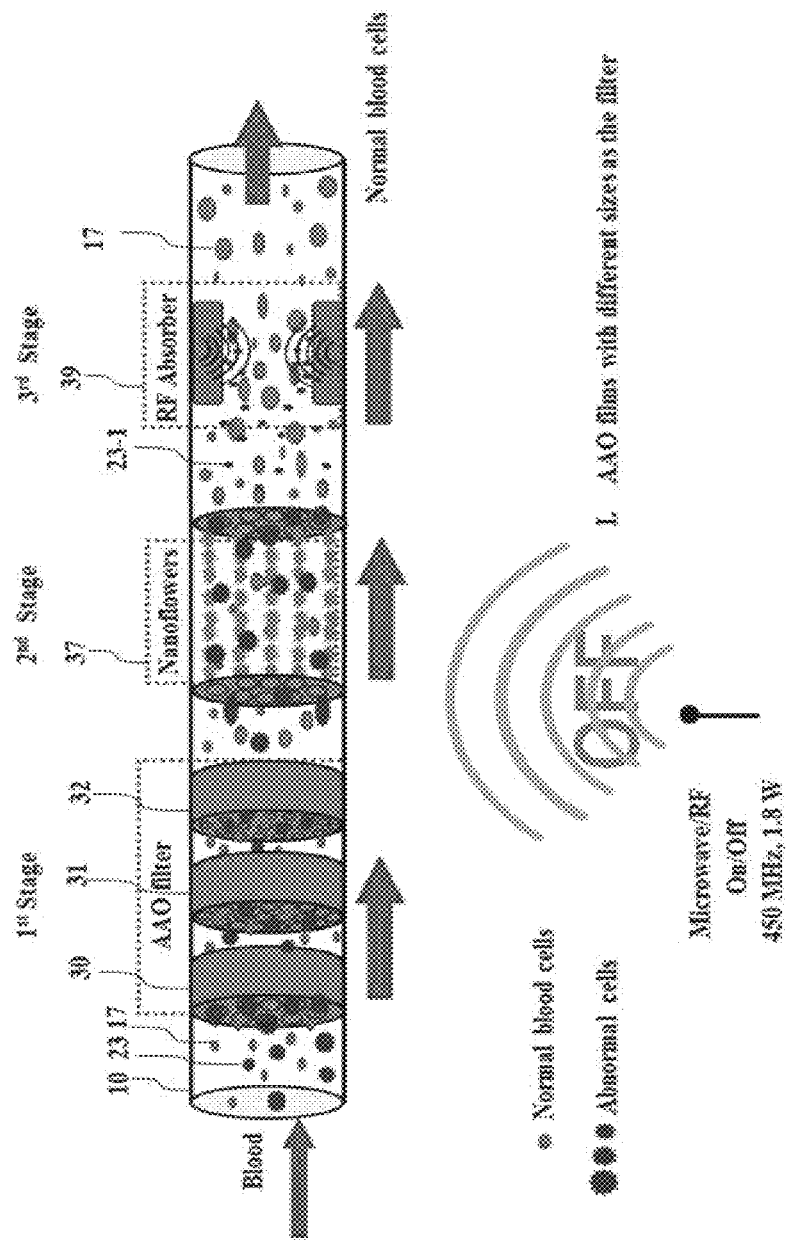
FIGS. 11 and 12 show providing a plurality of porous AAO filters or porous glass filters (stage 1)/nanoflowers (stage 2)/RF absorber (stage 3) according to Embodiment 4 of the present invention, and removing cancer cells by radiating an RF frequency of 450 MHz from an RF generator through turning on/off of an RF resonator of the microwave RF generator at regular time intervals.
Figure 12:
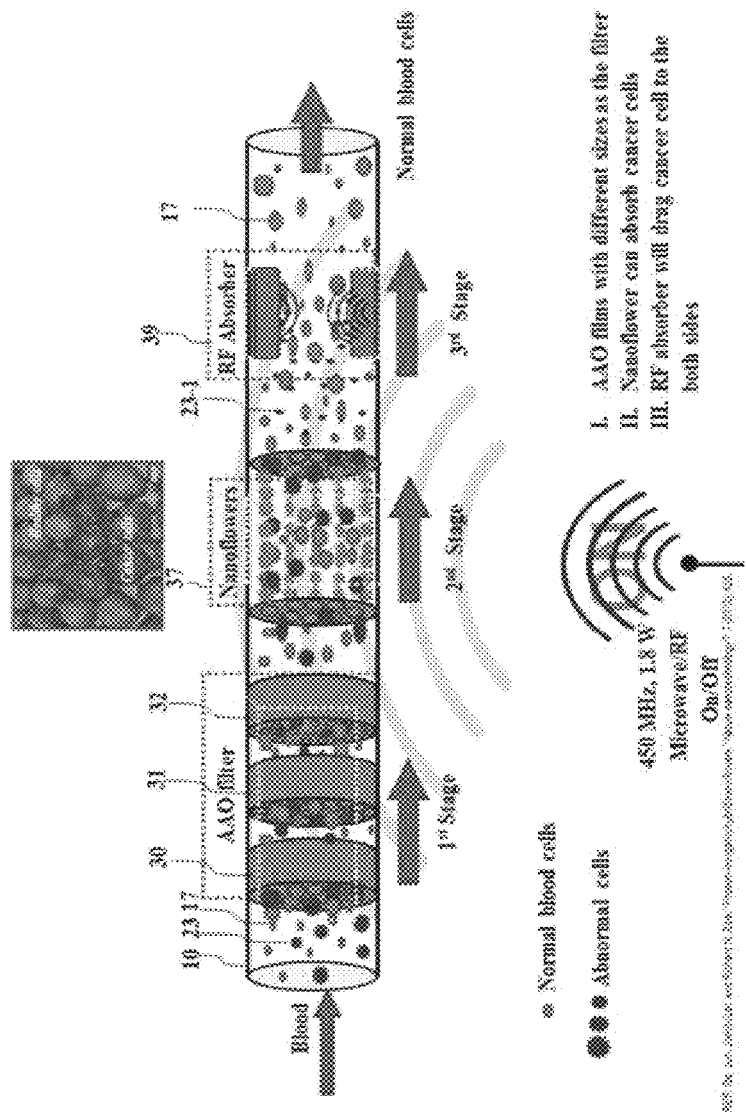

FIGS. 11 and 12 show that an apparatus according to Embodiment 4 of the present invention comprises a plurality of porous AAO filters or porous glass filters (stage 1)/nanoflowers (stage 2)/RF absorber (stage 3) and removes cancer cells by radiating a 450 MHz RF frequency from an RF generator through turning on/off of an RF resonator of a microwave RF generator at regular time intervals.

The microwave therapy apparatus for treating blood cancer according to Embodiment 4 of the present invention comprises: a plurality of porous anodic aluminum oxide (AAO) filters or a plurality of porous glass filters 30, 31 and 32 provided in a dialyzer of a hemodialysis apparatus, which is connected to a blood tube; a nanoflower filter 37 provided downstream of the plurality of porous anodic aluminum oxide (AAO) filters or the plurality of porous glass filters 30, 31 and 32 and configured to remove cancer cells from the blood tube connected to the artery of the cancer patient; and an RF absorber 39 provided downstream of the nanoflower filter and configured to attract the cancer cells thereto by generating a frequency of a predetermined band. The apparatus circulates and supplies, the blood, from which the cancer cells have been removed by the RF frequency and which includes normal blood cells that passed through the filters 30, 31, 32 and 37, to the blood tube 10 connected to the vein of the blood cancer patient in the blood flow direction (artery—vein).

The microwave therapy apparatus for treating blood cancer allows the cancer cells to adhere to the nanoflower filter, and further comprises a microwave RF generator configured to remove the cancer cells by radiating an RF frequency through turning on/off of an RF resonator of the RF generator.

Using a hemodialysis method, the plurality of porous anodic aluminum oxide (AAO) filters 30, 31 and 32 allow normal blood cells having a smaller pore diameter than cancer cells to pass, and filters abnormal blood cells including cancer cells having a larger diameter than the normal blood cells. When the diameter size of cancer cells is equal to or smaller than the size of normal blood cells, the cancer cells are removed by radiating an RF frequency through turning on/off of an RF resonator of a microwave RF generator at regular time intervals.

The plurality of porous anodic aluminum oxide (AAO) filters 30, 31 and 32 comprises porous anodic aluminum oxide (AAO) filters containing a plurality of pores having gradually decreasing diameters smaller than the diameter of cancer cells.

Specifically, three porous anodic aluminum oxide filters having different pore diameters smaller than the diameter of cancer cells are used.

The three porous anodic aluminum oxide (AAO) filters include a first porous anodic aluminum oxide filter 30 having a first pore diameter, a second porous anodic aluminum oxide filter having a second pore diameter smaller than the first pore diameter, and a third porous anodic aluminum oxide filter 32 having a third pore diameter smaller than the second pore diameter, and the first pore diameter, the second pore diameter and the third pore diameter are hole sizes of 60 μm, 30 μm and 10 μm, respectively.

After hemodialysis, the plurality of porous anodic aluminum oxide filters 30, 31 and 32 is separated from the dialyzer and replaced with a plurality of porous anodic aluminum oxide filters which is harmless to the human body.

The plurality of porous glass filters 30,31 and 32 comprises porous glass filters containing a plurality of pores having gradually decreasing diameters smaller than the diameter of cancer cells. For example, three porous glass filters having different pore diameters smaller than the diameter of cancer cells are used.

The three porous glass filters 30, 31 and 32 include a first porous glass 30 having a first pore diameter, a second porous glass filter 31 having a second pore diameter smaller than the first pore diameter, and a third porous glass filter 32 having a third pore diameter smaller than the second pore diameter, and the first pore diameter, the second pore diameter and the third pore diameter are holes sizes of 60 μm, 30 μm and μm, respectively.

After hemodialysis, the plurality of porous glass filters 30, 31 and 32 is separated from the dialyzer and replaced with a plurality of new (fresh) porous anodic aluminum oxide filters which is harmless to the human body.

When the size of cancer cells is equal to or smaller than the size of normal blood cells, the cancer cells are adhered to the nanoflower filter from the blood tube, connected to the artery of the cancer patient, to the nanoflower filter 37 provided in the dialyzer of the hemodialysis apparatus.

Outside the blood tube, a 450 MHz RF frequency is radiated through turning on/off of an RF resonator of a 1.8 W microwave RF generator at regular time intervals to remove cancer cells.

The nanoflower filter 37 is impregnated with gold (Au) to increase the reaction rate, and allows abnormal cells (i.e., cancer cells) to adhere thereto. After hemodialysis of the cancer patient, the nanoflower filter to which the cancer cells adhered is separated from the dialyzer and replaced with a new fresh nanoflower filter.

The RF absorber 39 is provided on the upper side and lower side of the blood tube in an RF shield box in the hemodialyzer. The cancer cells are removed by attraction to the RF absorber through generation of an RF frequency corresponding to an integer multiple of 13.56 MHz (x k=1, 2, 3 or 4), that is, an RF frequency of 13.56 MHz, 27.12 MHz, 40.68 MHz, or 54.12 MHz. After hemodialysis, the RF absorber is removed.

A microwave therapy method for treating blood cancer according to Embodiment 4 of the present invention comprises steps of: (a) providing a plurality of porous anodic aluminum oxide (AAO) filters or a plurality of porous glass filters in a dialyzer of a hemodialysis apparatus, to which blood is supplied from a blood tube connected to the artery of a leukemia patient when blood is circulated in the blood flow direction by operation of a blood pump during hemodialysis, allowing normal blood cells having a smaller diameter than cancer cells to pass through the filters, and filtering, by the filters, abnormal blood cells including cancer cells having a larger diameter than the normal blood cells; (b) providing a nanoflower filter downstream of the plurality of AAO filters or the plurality of porous glass filters provided in the dialyzer of the hemolysis apparatus, and allowing the cancer cells to adhere to the nanoflower filter; (c) removing the cancer cells by radiating an RF frequency through turning on/off of an RF resonator of a microwave RF generator at regular intervals; and (d) attracting the cancer cells to an RF absorber, provided downstream of the nanoflower, through generation of a frequency of a predetermined band by the RF absorber, and removing the RF absorber having the cancer cells attracted thereto, wherein the blood, from which the cancer cells have been removed and which includes the normal blood cells, is circulated and supplied to a blood tube connected to the vein of the cancer patient in the blood flow direction.

When the size of cancer cells is equal to or smaller than the size of normal blood cells, the method further comprises a step of removing the cancer cells in the filters provided in the dialyzer of the hemolysis apparatus, from the blood tube connected to the artery of the cancer patient, by radiating an RF frequency through turning on/off of an RF resonator of a 1.8 W RF microwave RF generator at regular time intervals.

The RF absorber is provided on the upper side and lower side of the blood tube in an RF shield box in the hemodialyzer, and the method further comprises a step of removing the cancer cells by attraction to the RF absorber through generation of an RF frequency corresponding to an integer multiple of 13.56 MHz (x k=1, 2, 3 or 4), that is, an RF frequency of 13.56 MHz, 27.12 MHz, 40.68 MHz, or 54.12 MHz, by the RF absorber, and removing the RF absorber after hemodialysis. In addition, the RF absorber may be used at least one frequency within a frequency range of 13.56 MHz to 54.12 MHz, but is not limited thereto.

The method comprises a step of removing the plurality of porous anodic aluminum oxide (AAO) filters or the plurality of porous glass filters, the nanoflower filters having the cancer cells adhered thereto, and the RF absorber having the cancer cells attracted thereto, after hemodialysis.

The method further comprises a step of providing an RF shield box (RF shield room) configured to shield the blood tube 10 in the dialyzer of the hemodialysis apparatus. The RF shield box is made of a plastic, aluminum, ceramic or rubber material, and shields frequencies outside the hemodialyzer using the RF shielding material. The RF shield box is provided in the form of a rectangular box shape, a cylindrical shape, a polygonal shape such as a pentahedral, hexahedral, heptahedral or octahedral shape, in the dialyzer of the hemodialysis apparatus, and the RF shield material shields an RF frequency in the MHz to GHz band. The RF shield material comprises silver (Ag) as a screening material. Also, the RF shield material comprises an Aaronia shield material that shields an RF frequency in a band of 100 MHz to 10 GHz, or Aaronia X-steel that uses stainless steel as a screening material and shields an RF frequency in a band of 1 MHz to 50 GHz. After hemodialysis, the RF absorber is removed.

Figure 13:
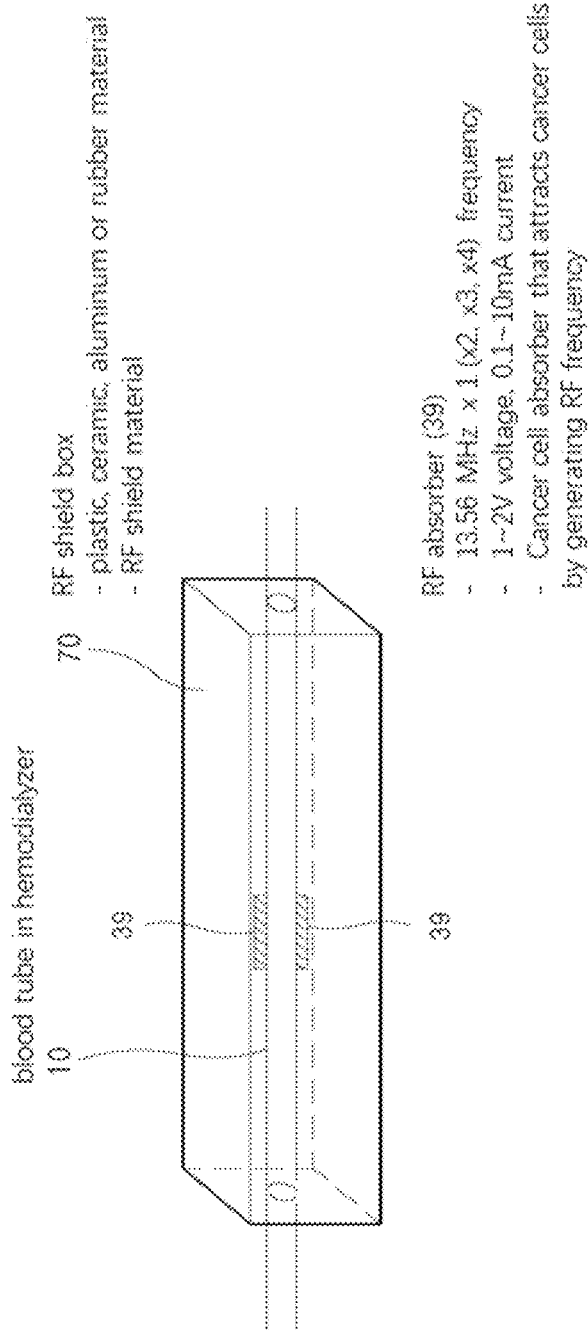
FIG. 13 shows a process of removing cancer cells by attraction to an RF absorber through generation of an RF frequency of 13.56 MHz, 27.12 MHz, 40.68 MHz or 54.12 MHz RF by the RF absorber provided on the upper side and lower side of a blood tube in an RF shield box in a hemodialyzer.

FIG. 13 shows a process of removing cancer cells by attraction to an RF absorber through generation of an RF frequency of 13.56 MHz, 27.12 MHz, 40.68 MHz or 54.12 MHz RF by the RF absorber provided on the upper side and lower side of the blood tube in the RF shield box in the hemodialysis apparatus.

The hemodialysis apparatus comprises an RF shield box (RF shield room) 70 configured to shield the blood tube 10 in the dialyzer of the hemodialysis apparatus. The RF shield box 70 is made of a plastic, aluminum, ceramic or rubber material, and shields frequencies outside the hemodialyzer using the RF shield material. The RF shield box 70 is provided in the form of a rectangular box shape, a cylindrical shape, a polygonal shape such as a pentahedral, hexahedral, heptahedral or octahedral shape, in the dialyzer of the hemodialysis apparatus.

The RF shield material shields an RF frequency in the MHz to GHz band.

For example, the RF shield material comprises silver (Ag) as a screening material. Also, the RF shield material may comprise an Aaronia shield material that shields an RF frequency in a band of 100 MHz to 10 GHz, or Aaronia X-steel that uses stainless steel as a screening material and shields an RF frequency in a band of 1 MHz to 50 GHz.

The RF absorber 39 is provided on the upper and lower sides of the blood tube 10 in the RF shield box 70 in the hemodialyzer. The RF absorber 39 generates an RF frequency of 13.56 MHz, 27.12 MHz, 40.68 MHz or 54.12 MHz, which is an integer multiple of 13.56 MHz (x k=1, 2, 3 or 4) in the ISM band. That is, the RF absorber 39 generates an RF frequency in the range of 13.56 MHz to 54.24 MHz using a current of 0.1 to 10 mA and a voltage of 1 to 2 V. The RF absorber 39 functions as a cancer cell absorber that attracts cancer cells passing through the blood tube in the hemodialyzer by generating an RF frequency corresponding to an integer multiple of 13.56 MHz (x k=1, 2, 3 or 4).

The RF absorber means an RF cancer absorber.

Since the resonant frequency of normal cells and the resonant frequency of cancer cells are different depending on the solution composition and genetic characteristics of blood, cancer cells can be removed by radiating an RF frequency.

The microwave therapy apparatus for leukemia treatment according to the present invention, which is less harmful to the human body, is less harmful to the human body than existing chemotherapy or radiotherapy and may remove cancer cells. Thus, it may be applied for treatment of blood cancer, such as leukemia, and cancer.

Figure 14:
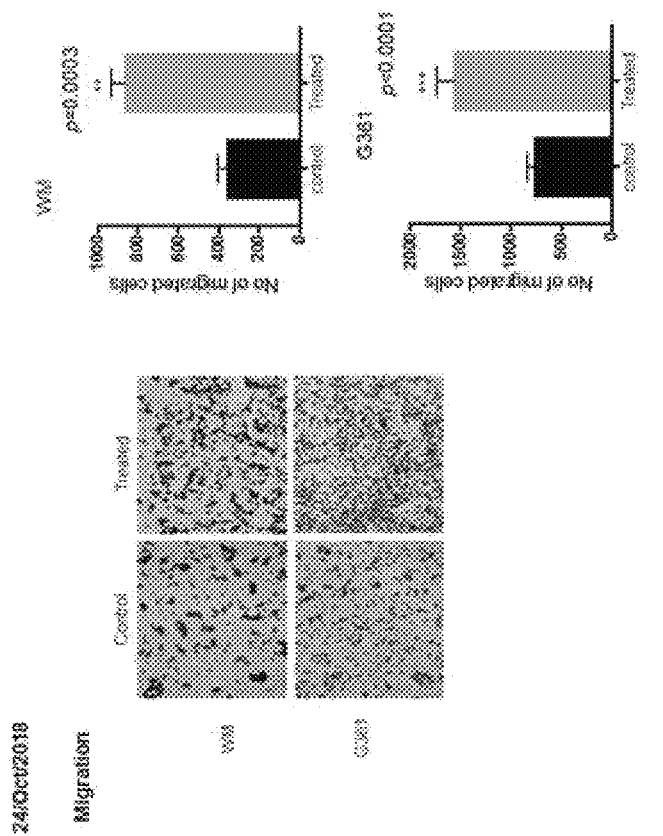
FIG. 14 shows the results of analyzing the migration of skin cancer WM and G361 cells on Oct. 24, 2018 before analyzing the blood cancer cells in solution, and compares a treated group (in which an RF frequency was used for 20 hours) with a control group (no RF frequency was used).

FIG. 14 shows the results of analyzing the migration of skin cancer WM and G361 cells on Oct. 24, 2018 before analyzing the blood cancer cells in solution, and compares a treated group (in which an RF frequency was used for 20 hours) with a control group (no RF frequency was used).

From the results in FIG. 14 that shows the clinical test results of analyzing the migration of skin cancer WM and G361 cells on Oct. 24, 2018 before analyzing the blood cancer cells in solutions, and compares a treated group (in which an RF frequency was used for 20 hours) with a control group (no RF frequency was used), it can be seen that the skin cancer cells significantly migrated.

Figure 15:
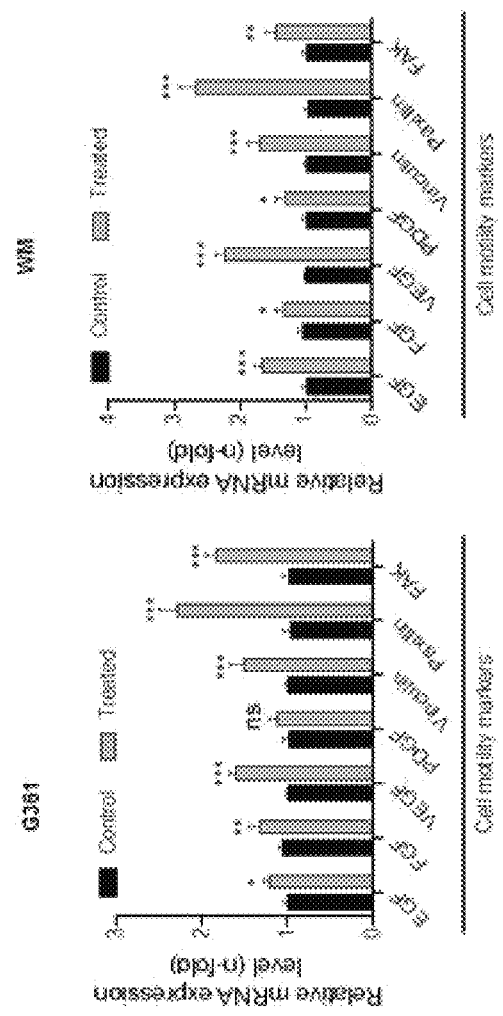
FIG. 15 shows the results of measuring the relative mRNA expression levels of qPC-cell gene biomarkers in skin cancer WM and G361 cells on Feb. 12, 2019, and compares a treated group (in which an RF frequency was used for 20 hours) with a control group (no RF frequency was used).

FIG. 15 shows the results of measuring the relative mRNA mobility level (mRNA export level from nucleus to cytoplasm) of qPC-cell gene biomarkers in skin cancer WM and G361 cells on Feb. 12, 2019, and compares a treated group (in which an RF frequency was used for 20 hours) with a control group (no RF frequency was used).

From the results of FIG. 15 that shows the results of measuring the relative mRNA mobility level of qPC-cell gene biomarkers in skin cancer WM and G361 cells on Feb. 12, 2019, and compares a treated group (in which an RF frequency was used for 20 hours) with a control group (no RF frequency was used), it can be seen that the skin cancer cells significantly migrated.

INDUSTRIAL APPLICABILITY

The microwave therapy apparatus and method for treating blood cancer have the following effects: i) cancer cells having a larger diameter than normal blood cells that are being circulated through the blood tube are filtered out by size filtration by the plurality of porous anodic aluminum oxide (AAO) filters and the plurality of porous glass filters provided in the dialyzer of the hemodialysis apparatus for blood cancer therapy of a leukemia patient; ii) when the diameter size of cancer cells is equal to or smaller than the size of normal blood cells, the cancer cells are caused to adhere to the nanoflower filter and are removed by radiating an RF frequency of 450 MHz through turning on/off of the RF resonator of the microwave RF generator at regular intervals; and iii) cancer cells are removed by attraction to the RF absorber through generation of an RF frequency of 13.56 MHz, 27.12 MHz, 40.68 MHz or 54.12 MHz by the RF absorber provided on the upper side and lower side of the blood tube in the RF shield box in the hemodialyzer.

The blood, from which the abnormal blood cells have been filtered out by hemodialysis, is circulated and supplied to the vein of the body of the leukemia patient in the blood flow direction (artery—vein), and the cancer cells are removed after hemodialysis of the leukemia patient.

The microwave therapy apparatus for leukemia treatment according to the present invention, which is less harmful to the human body, is less harmful to the human body than existing chemotherapy and radiotherapy, and may be used to treat blood cancer, such as leukemia, and cancer, by removing cancer cells.

Although the present invention has been described above with reference to preferred embodiments of the present invention, those skilled in the art can understand that the present invention can be variously modified and changed without departing from the technical spirit and scope of the present invention as defined in the appended claims.

What is claimed is:

1. A microwave therapy apparatus for blood cancer treatment comprising:
   a plurality of porous anodic aluminum oxide (AAO) filters or a plurality of porous glass filters provided in a dialyzer of a hemodialysis apparatus, which is connected to a blood tube;
   a nanoflower filter provided downstream of the plurality of porous anodic aluminum oxide (AAO) filters or the plurality of porous glass filters in the blood tube connected to an artery of a blood cancer patient; and
   an RF absorber provided downstream of the nanoflower filter and configured to attract cancer cells thereto by generating a frequency of a predetermined band,
   wherein the blood, from which the cancer cells have been removed by an RF frequency and which includes normal blood cells that passed through the nanoflower filter, is circulated and supplied to a blood tube connected to a vein of a body of the blood cancer patient.

2. The microwave therapy apparatus of claim 1, further comprising:
   a microwave RF generator configured to cause the cancer cells to adhere to the nanoflower filter and to remove the cancer cells by radiating the RF frequency through turning on/off of an RF resonator of an RF generator at regular time intervals.

3. The microwave therapy apparatus of claim 2, wherein the plurality of porous anodic aluminum oxide (AAO) filters allow normal blood cells having a smaller diameter than the cancer cells to pass by using a hemodialysis method, and filters abnormal blood cells including the cancer cells having a larger diameter than the normal blood cells, and when a diameter size of cancer cells is equal to or smaller than a size of the normal blood cells, the cancer cells are removed by radiating the RF frequency through turning on/off of the RF resonator of the microwave RF generator at regular time intervals.

4. The microwave therapy apparatus of claim 3, wherein the plurality of porous anodic aluminum oxide (AAO) filters comprises porous anodic aluminum oxide filters containing a plurality of pores having gradually decreasing pore diameters, and three porous anodic aluminum oxide (AAO) filters having different pore sizes smaller than a diameter of the cancer cells are used.

5. The microwave therapy apparatus of claim 4, wherein the three porous anodic aluminum oxide (AAO) filters comprise a first porous anodic aluminum oxide filter having a first pore diameter, a second porous anodic aluminum oxide filter having a second pore diameter smaller than the first pore diameter, and a third porous anodic aluminum oxide filter having a third pore diameter smaller than the second pore diameter, and the first pore diameter, the second pore diameter and the third pore diameter are hole sizes of 60, 30 and 10 µm, respectively.

6. The microwave therapy apparatus of claim 3, wherein the plurality of porous anodic aluminum oxide filters is separated from the dialyzer and replaced with a plurality of new porous anodic aluminum oxide filters which is harmless to a human body, after hemodialysis.

7. The microwave therapy apparatus of claim 1, wherein the plurality of porous glass filters comprises porous glass filters containing a plurality of pores having gradually decreasing diameters, and three porous glass filters having different pore diameters smaller than a diameter of the cancer cells are used.

8. The microwave therapy apparatus of claim 7, wherein the three porous glass filters comprise a first porous glass filter having a first pore diameter, a second porous glass filter having a second pore diameter smaller than the first pore diameter, and a third porous glass filter having a third pore diameter smaller than the second pore diameter, and the first pore diameter, the second pore diameter and the third pore diameter are hole sizes of 60, 30 and 10 µm, respectively.

9. The microwave therapy apparatus of claim 1, wherein the plurality of porous glass filters is separated from the dialyzer and replaced with a plurality of new porous glass filters which is harmless to a human body, after hemodialysis.

10. The microwave therapy apparatus of claim 1, wherein, when a size of cancer cells is equal to or smaller than a size of normal blood cells, the cancer cells are adhered to the nanoflower filter, provided in the dialyzer of the hemodialysis apparatus, from the blood tube connected to the artery of the blood cancer patient, and the cancer cells are removed by radiating the RF frequency of 450 MHz through turning on/off of a 1.8 W microwave RF resonator at regular time intervals.

11. The microwave therapy apparatus of claim 1, wherein the nanoflower filter is impregnated with gold (Au) to increase reaction rate, and allows abnormal cells to adhere thereto, and the nanoflower filter having the cancer cells adhered thereto is separated from the dialyzer and replaced with a new nanoflower filter, after hemodialysis of the blood cancer patient.

12. The microwave therapy apparatus of claim 1, wherein the RF absorber is provided on the upper side and lower side of the blood tube in an RF shield box in the dialyzer, the cancer cells are removed by attraction to the RF absorber through generation of an RF frequency of 13.56 MHz, 27.12 MHz, 40.68 MHz or 54.12 MHz by the RF absorber, and the RF absorber is removed after hemodialysis.

13. The microwave therapy apparatus of claim 1, wherein the RF absorber uses at least one frequency within a frequency range of 13.56 MHz to 54.12 MHz.

14. The microwave therapy apparatus of claim 1, further comprising:
an RF shield box (RF shield room) configured to shield the blood tube 10 in the dialyzer of the hemodialysis apparatus, the RF shield box is made of a plastic, aluminum, ceramic or rubber material, and shields frequencies outside a hemodialyzer using an RF shield material, the RF shield box is provided in a form of a rectangular box shape, a cylindrical shape, a polygonal shape such as a pentahedral, hexahedral, heptahedral or octahedral shape, in the dialyzer of the hemodialysis apparatus,
the RF shield material shields an RF frequency in the MHz to GHz band,
the RF shield material comprises silver (Ag) as a screening material, or comprises an Aaronia shield material that shields an RF frequency in a band of 100 MHz to 10 GHz, or Aaronia X-steel that comprises stainless steel as a screening material and shields an RF frequency in a band of 1 MHz to 50 GHz, and the RF absorber is removed after hemodialysis.

15. A microwave therapy method for blood cancer treatment comprising:
(a) providing a plurality of porous anodic aluminum oxide (AAO) filters or a plurality of porous glass filters in a dialyzer of a hemodialysis apparatus, to which blood is supplied from a blood tube connected to an artery of a blood cancer patient when blood is circulated in a blood flow direction by operation of a blood pump during hemodialysis, allowing normal blood cells having a smaller diameter than cancer cells to pass through the filters, and filtering, by the filters, abnormal blood cells including the cancer cells having a larger diameter than the normal blood cells;
(b) providing a nanoflower filter downstream of the plurality of AAO filters or the plurality of porous glass filters provided in the dialyzer of a hemolysis apparatus, and allowing the cancer cells to adhere to the nanoflower filter;
(c) removing the cancer cells by radiating an RF frequency through turning on/off of an RF resonator of a microwave RF generator at regular intervals; and
(d) adhering the cancer cells to an RF absorber, provided downstream of the nanoflower filter, by generation of a frequency of a predetermined band by the RF absorber, and removing the RF absorber,
wherein the blood, from which the cancer cells have been removed and which includes the normal blood cells, is circulated and supplied to a blood tube connected to a vein of a body of the blood cancer patient in the blood flow direction.

16. The microwave therapy method of claim 15, wherein, when a size of cancer cells is equal to or smaller than a size of normal blood cells, the method further comprises removing the cancer cells in the filters provided in the dialyzer of the hemolysis apparatus, from the blood tube connected to the artery of the blood cancer patient, by radiating the RF frequency through turning on/off of an RF resonator of a 1.8 W RF microwave RF generator.

17. The microwave therapy method of claim 15, wherein the RF absorber is provided on the upper side and lower side of the blood tube in an RF shield box in a hemodialyzer, and the method further comprises removing the cancer cells by attraction to the RF absorber through generation of an RF frequency of 13.56 MHz, 27.12 MHz, 40.68 MHz, or 54.12 MHz by the RF absorber, and removing the RF absorber after hemodialysis.

18. The microwave therapy method of claim 15, wherein the RF absorber uses at least one frequency within a frequency range of 13.56 MHz to 54.12 MHz.

19. The microwave therapy method of claim 15, further comprising:
removing the plurality of porous anodic aluminum oxide (AAO) filters or the plurality of porous glass filters, the nanoflower filter having the cancer cells adhered thereto, and the RF absorber having the cancer cells attracted thereto, after hemodialysis.

* * * * *